(12) United States Patent
Peters et al.

(10) Patent No.: US 8,003,854 B2
(45) Date of Patent: Aug. 23, 2011

(54) GRG32: A NOVEL EPSP SYNTHASE GENE CONFERRING HERBICIDE RESISTANCE

(75) Inventors: Cheryl Peters, Raleigh, NC (US); Brian Vande Berg, Durham, NC (US); Brian Carr, Raleigh, NC (US); Daniel John Tomso, Bahama, NC (US)

(73) Assignee: Athenix Corp., Morrisville, NC (US)

( * ) Notice: Subject to any disclaimer, the term of this patent is extended or adjusted under 35 U.S.C. 154(b) by 890 days.

(21) Appl. No.: 11/769,255

(22) Filed: Jun. 27, 2007

(65) Prior Publication Data

US 2007/0300325 A1  Dec. 27, 2007

Related U.S. Application Data

(60) Provisional application No. 60/816,677, filed on Jun. 27, 2006.

(51) Int. Cl.
*C12N 15/82* (2006.01)
*C12N 15/52* (2006.01)

(52) U.S. Cl. ............... 800/300; 435/252.3; 435/320.1; 435/419; 536/23.2; 800/288; 800/295

(58) Field of Classification Search .................. None
See application file for complete search history.

(56) References Cited

U.S. PATENT DOCUMENTS

2005/0223436 A1  10/2005  Lin et al.

FOREIGN PATENT DOCUMENTS

| WO | WO 92/04449 A1 | 3/1992 |
|---|---|---|
| WO | WO 2005/083065 A1 | 9/2005 |
| WO | WO 2006/012080 * | 2/2006 |
| WO | WO 2006/012080 A2 | 2/2006 |

OTHER PUBLICATIONS

Dill, G.M., et al., "Glyphosate-resistant Crops: History, Status and Future," *Pest Manag Sci*, Mar. 2005, pp. 219-224, vol. 61, No. 3.
Liu, Z., et al., "Cloning and Expression of a 5-enolpyruvylshikimate-3-phosphate Synthase Gene from *Halomonas variabilis*," *DNA Sequence*, Jun. 2006, pp. 208-214, vol. 17, No. 3.
Saroha, M.K., et al., "Glyphosate-tolerant Crops: Genes and Enzymes," *J. Plant Biochemistry & Biotechnology*, Jul. 1998, pp. 65-72, vol. 7.
Sun, Y.-C. et al., "Novel AroA with High Tolerance to Glyphosate, Encoded by a Gene of *Pseudomonas putida* 4G-1 Isolated from an Extremely Polluted Environment in China," *Appl. Environ. Microbiol.*, Aug. 2005, pp. 4771-4776, vol. 71, No. 8.
NCBI Report for Accession No. AAM36518, Direct Submission on Nov. 28, 2001.
NCBI Report for Accession No. AAM40886, Direct Submission on Nov. 28, 2001.
NCBI Report for Accession No. BAE69021, Direct Submission on Nov. 16, 2004.
NCBI Report for Accession No. YP_363422, Direct Submission on Jun. 16, 2005.

* cited by examiner

*Primary Examiner* — David H Kruse
(74) *Attorney, Agent, or Firm* — Destiny M. Davenport

(57) ABSTRACT

Compositions and methods for conferring herbicide resistance to bacteria, plants, plant cells, tissues and seeds are provided. Compositions include nucleic acid molecules encoding herbicide resistance or tolerance polypeptides, vectors comprising those nucleic acid molecules, and host cells comprising the vectors. The nucleotide sequences of the invention can be used in DNA constructs or expression cassettes for transformation and expression in organisms, including microorganisms and plants. Compositions also comprise transformed bacteria, plants, plant cells, tissues, and seeds. In particular, the present invention provides for isolated nucleic acid molecules comprising the nucleotide sequence set forth in SEQ ID NO:1 or 14, a nucleotide sequence encoding the amino acid sequence shown in SEQ ID NO:2, the herbicide resistance nucleotide sequence deposited in a bacterial host as Accession Nos. NRRL B-30931, as well as variants and fragments thereof.

15 Claims, 3 Drawing Sheets

```
                          *         200         *         220         *         240
GRG32          : PLH D A    S QV SAVLL  LY QGE SVT -----H  DY  MI AFG  E   : 213
X_axonopodis_pv: ALH D V    S QV SAVLL  LY QGE SVT -----H  LY  ML SAFG E D : 214
X_campestris_pv: ALQ T A    S QV SAVLL  LY TGE SVS -----H  YT  ML SAFG E A : 214
X_campestris_pv: ALH D V    S QV SAVLL  LY QGE SVT -----H  DY  ML SAFG E D : 214
X_oryzae_pv._or: ALH D V    S QV SAVLL  LY QGE SVT -----H  DY  ML SAFG D D : 214
X_fastidiosa_9a: LLH D T    S QV SAVLL  LY RNE VVR -----H  YT  MI TAFG D D : 227
X_fastidiosa_An: LLP D I    S QV SAVLL  LY RNE VVR -----H  YT  MI TAFG D D : 215
X_fastidiosa_Te: LLP D I    S QV SAVLL  LY RNE VVR -----H  YT  MI TAFG D D : 227
CP4            : TPTP  RV   S Q  SAVLL  NTPGI TVI -----IM  HT  ML QGFGAN T : 215
B_Subtilis     : SLK D V    S QI SAVLL  LQ EGT TVT -----HK  HT  ML SAFG K S : 206
E_coli         : FTG NVDVDGSVSSQFLTALLMTAPL PED VIRIKGDLVSK YI  TLNLMKTFG E E : 216
Zea_maize      : LPG KVKL GSISSQYLSALLM APL LGDVE IEIIDKLISI YVEMTL LMERFG KAE : 225

*         260         *         280         *         300
GRG32          : FSPGK-----ARL G   RATD A  A F SAA    A S I  A TDRQ    --R : 266
X_axonopodis_pv: FSPGK-----ARL G   RATD A  A F SAA    A S V  E VVLRA    --R : 267
X_campestris_pv: FSPGQ-----ARL G   RATD A  A F SAA    A S V  G VTLRA    --R : 267
X_campestris_pv: FSPGK-----ARL G   RATD A  A F SAA    A S V  E VVLRA    --R : 267
X_oryzae_pv._or: FSPGS-----ARL G   RATD A  A F SAA    A S V D E VVLRA    --R : 267
X_fastidiosa_9a: VSTGC-----ARL G   CATD T  A F SAA    A S I  D ITLRA    --R : 280
X_fastidiosa_An: VSTGC-----ARL G   CATN T  A F SAA    A S I  D ITLRA    --R : 268
X_fastidiosa_Te: VSTGC-----VRL G   CATN T  A F SAA    A S I  D ITLRA    --R : 280
CP4            : VETDADGVRTIRLEGRG TGQV D G P STA P  A L V  D VTLLN L    --T : 273
B_Subtilis     : EDQTS-----VS AG   TAAD F G I SAA    AAGA V N  RIVLKN     --T : 259
E_coli         : N----QHYQQFV  G   SYQSPGTY VEGDASSAS F AAAIK GT RWTG  R SMQG : 272
Zea_maize      : HS---DSWDRFY  G   YKSPKNAY VEGDASSAS F AGAAIT GT VWEGC TTSLQG : 282
```

FIG. 1A

```
                          *         320         *         340         *         360
GRG32            : T   AALRLMGAD REE HAEQ G AVA   V RHAP HGAE PEAL PDM D F ALF  : 326
X_axonopodis_pv  : T   AALRLMGAD GEE HAEH G PVA   H RYAP RGAQ PEAL PDM D F ALF  : 327
X_campestris_pv  : T   AALRLMGAD VED HAEH G PVA   R RYAP RGAQ PEAL PDM D F ALF  : 327
X_campestris_pv  : T   AALRLMGAE SEE HAEH G PVA   R RYAP RGAQ PEAL PDM D P ALF  : 327
X_oryzae_pv._or  : T   AALRLMGAD SEE HAEH G PVA   R RYAP RGAQ PEAL PDM D F ALF  : 327
X_fastidiosa_9a  : I   TVLRLMGAM IVES RHEQ G PVV   R RYAP QGTR PEDL AIM D F ALF  : 340
X_fastidiosa_An  : I   TVLRLMGAD IVES CHEQ G PVA   R RYAP QGTR PEDL PDM D F VLF  : 328
X_fastidiosa_Te  : I   TVLRLMGAD IVES RHEQ G DVA   R RYAS QGTR PEDL PDM D F ALF  : 340
CP4              : T   LTLQEMGAD IEVI PRLA G DVA   P RSST KGVT PEDRAPSM D Y ILA  : 333
B_Subtilis       : T   DVLQNMGAK LEIKPSADS A PYG   I ETSS KAVE GGDI PRL D I ILA  : 319
E_coli           : DIRFADV EKMGAT CWG  DYISCT------------RGELNAIDMD NH PDAAMT AT : 320
Zea_maize        : DVKFAEV EMMGAK TWTETSVTVTG---PP-REPFGRKHLKAIDVN NKMPDVAMT A  : 338

*         380         *         400         *         420
GRG32            : AAA QGNT VPGA  RVKES RLA MA GL S GVQ D TE GAT H G--------HE : 379
X_axonopodis_pv  : AAA SGCT VTGA  RVKES RLA MA GL T GIQ D TP GAT H G--------S  : 379
X_campestris_pv  : AAA RGDT VSGA  RVKES RLA MA GL A GIV D TP GAT H G--------T  : 379
X_campestris_pv  : AAA SGCT VTGA  RVKES RLA MA GL T GVQ D TP GAT H G--------S  : 379
X_oryzae_pv._or  : ATA SGCT VTGA  RVKES RLA MA GL T GVQ D TP GAT H G--------S  : 379
X_fastidiosa_9a  : AAA EGCT VSGA  RVKES RLA MV GL V GVQ D TA GAT H G--------P  : 392
X_fastidiosa_An  : AAA EGCT VSGA  RVKES RLA MV GL V GVQ D TA GAT H G--------P  : 380
X_fastidiosa_Te  : AAA EGCT VSGA  RVKES RLA MV GL V GVQ D TA GAT H G--------P  : 392
CP4              : A PAEGAT MNGLE RVKES RLS VANGL LNG VDCD GETSLVW RPDGKGLG-N  : 392
B_Subtilis       : LATQAEGTT IKDA  KVKET RIDTVV EL K GAE EPTA GMKVY KQT------L  : 373
E_coli           : ALFAKGTT RLRNIYNW RVKET RLF MA ED K GAE E GH YIR TPPE-------K  : 373
Zea_maize        : VALFADGPTAIRDV SW RVKETERMV IR ELTK GAS E GP YCI TPPE-------K  : 391
```

FIG. 1B

```
                                *         440         *         460         *         480
GRG32           : GSGTIES GDHRI MA AI GQ  SGEVRIN IAN  TSFPNFDG ARTAGFNLG---- : 435
X_axonopodis_pv : GSGVIES GDHRI MA AI GQ  MGQVQVN VAN  TSFPGFDT AQDVGFGLETAGH : 439
X_campestris_pv : GSGVIES GDHRI MA AI GQ  TGTVQVN VAN  TSFPGFDS AQGAGFGLSARP- : 438
X_campestris_pv : GSGVIES GDHRI MA AI GQ  TGQVQVN VAN  TSFPGFDT AQGAGFGLETAGR : 439
X_oryzae_pv._or : GSGVIES GDHRI MA AI GQ  SGSVRVN VAN  TSFPGFDT AQGAGFGLEAAES : 439
X_fastidiosa_9a : GHGTINS GDHRI MA SI GQ  VSTVRIE VAN  TSFPDYET ARSAGFGLEVYCD : 452
X_fastidiosa_An : GHGTINS GDHRI MA SI GQ  VSTVRIE VAN  TSFPNYET ARSAGFGLEVYCD : 440
X_fastidiosa_Te : GHGTINS GDHRI MA SI GQ  VSTVRIE VAN  TSFPDYET ARSAGFGLEVYCD : 452
CP4             : ASGAAVAT LDHRI MS LVMGL  ENPVTVD ATM  TSFPEFMD MAGLGAKIELSDT : 452
B_Subtilis      : KGGAAVSS GDHRI GMMLGI SC  EEPIEIEHTDA HVSYPTFFEHLNKLSKKS----- : 428
E_coli          : NFAEIATYNDHRM MC SIVALS-DTPVTIL PKCT KTFPDYFEQLARISQAA----- : 427
Zea_maize       : NVTAIDTYDDHRM MA SI ACA-EVPVTIR PGCTRKTFPDYFD LSTFVKN------ : 444

GRG32           : ---  :  -
X_axonopodis_pv : R--  : 440
X_campestris_pv : ---  :  -
X_campestris_pv : R--  : 440
X_oryzae_pv._or : G--  : 440
X_fastidiosa_9a : PA-  : 454
X_fastidiosa_An : PA-  : 442
X_fastidiosa_Te : PA-  : 454
CP4             : KAA  : 455
B_Subtilis      : ---  :  -
E_coli          : ---  :  -
Zea_maize       : ---  :  -
```

FIG. 1C

GRG32: A NOVEL EPSP SYNTHASE GENE CONFERRING HERBICIDE RESISTANCE

CROSS REFERENCE TO RELATED APPLICATION

This application claims the benefit of U.S. Provisional Application Ser. No. 60/816,677, filed Jun. 27, 2006, the contents of which are herein incorporated by reference in their entirety.

REFERENCE TO SEQUENCE LISTING SUBMITTED ELECTRONICALLY

The official copy of the sequence listing is submitted electronically via EFS-Web as an ASCII formatted sequence listing with a file named "325171_SequenceListing.txt", created on Jun. 22, 2007, and having a size of 51 kilobytes and is filed concurrently with the specification. The sequence listing contained in this ASCII formatted document is part of the specification and is herein incorporated by reference in its entirety.

FIELD OF THE INVENTION

This invention provides novel genes encoding 5-enolpyruvylshikimate-3-phosphate (EPSP) synthase that provide herbicide resistance. These genes are useful in plant biology, crop breeding, and plant cell culture.

BACKGROUND OF THE INVENTION

N-phosphonomethylglycine, commonly referred to as glyphosate, is an important agronomic chemical. Glyphosate inhibits the enzyme that converts phosphoenolpyruvic acid (PEP) and 3-phosphoshikimic acid to 5-enolpyruvyl-3-phosphoshikimic acid. Inhibition of this enzyme (5-enolpyruvylshikimate-3-phosphate synthase; referred to herein as "EPSP synthase") kills plant cells by shutting down the shikimate pathway, thereby inhibiting aromatic acid biosynthesis.

Since glyphosate-class herbicides inhibit aromatic amino acid biosynthesis, they not only kill plant cells, but are also toxic to bacterial cells. Glyphosate inhibits many bacterial EPSP synthases, and thus is toxic to these bacteria. However, certain bacterial EPSP synthases have a high tolerance to glyphosate.

Plant cells resistant to glyphosate toxicity can be produced by transforming plant cells to express glyphosate-resistant bacterial EPSP synthases. Notably, the bacterial gene from *Agrobacterium tumefaciens* strain CP4 has been used to confer herbicide resistance on plant cells following expression in plants. A mutated EPSP synthase from *Salmonella typhimurium* strain CT7 confers glyphosate resistance in bacterial cells, and confers glyphosate resistance on plant cells (U.S. Pat. Nos. 4,535,060; 4,769,061; and 5,094,945).

U.S. Pat. No. 6,040,497 reports mutant maize EPSP synthase enzymes having substitutions of threonine to isoleucine at position 102 and proline to serine at position 106 (the "TIPS" mutation). Such alterations confer glyphosate resistance upon the maize enzyme. A mutated EPSP synthase from *Salmonella typhimurium* strain CT7 confers glyphosate resistance in bacterial cells, and is reported to confer glyphosate resistance upon plant cells (U.S. Pat. Nos. 4,535,060; 4,769, 061; and 5,094,945). He et al. ((2001) *Biochim et Biophysica Acta* 1568:1-6) have developed EPSP synthases with increased glyphosate tolerance by mutagenesis and recombination between the *E. coli* and *Salmonella typhimurium* EPSP synthase genes, and suggest that mutations at position 42 (T42M) and position 230 (Q230K) are likely responsible for the observed resistance.

Subsequent work (He et al. (2003) *Biosci. Biotech. Biochem.* 67:1405-1409) shows that the T42M mutation (threonine to methionine) is sufficient to improve tolerance of both the *E. coli* and *Salmonella typhimurium* enzymes. These enzymes contain amino acid substitutions in their active sites that prevent the binding of glyphosate without affecting binding by PEP or S3P. Mutations that occur in the hinge region between the two globular domains of EPSP synthase have been shown to alter the binding affinity of glyphosate but not PEP (He et al., 2003, supra). Therefore, such enzymes have high catalytic activity, even in the presence of glyphosate.

Due to the many advantages herbicide resistance plants provide, methods for identifying herbicide resistance genes with glyphosate resistance activity are desirable.

SUMMARY OF INVENTION

Compositions and methods for conferring herbicide resistance or tolerance to bacteria, plants, plant cells, tissues and seeds are provided. Compositions include nucleic acid molecules encoding herbicide resistance or tolerance polypeptides, vectors comprising those nucleic acid molecules, and host cells comprising the vectors. Compositions also include antibodies to the herbicide resistance or tolerance polypeptides. As noted the nucleotide sequences of the invention can be used in DNA constructs or expression cassettes for transformation and expression in organisms, including microorganisms and plants. Compositions also comprise transformed bacteria, plants, plant cells, tissues, and seeds. In addition, methods are provided for producing the polypeptides encoded by the synthetic nucleotides of the invention.

In particular, isolated nucleic acid molecules and variants thereof encoding herbicide resistance- or tolerance polypeptides are provided. Additionally, amino acid sequences and variants thereof encoded by the polynucleotides that confer herbicide resistance or tolerance are encompassed. In particular, the present invention provides for isolated nucleic acid molecules comprising the nucleotide sequence set forth in SEQ ID NO:1 or 14, a nucleotide sequence encoding the amino acid sequence shown in SEQ ID NO:2, the herbicide resistance nucleotide sequence deposited in a bacterial host as Accession No. NRRL B-30931, as well as variants and fragments thereof. Nucleotide sequences that are complementary to a nucleotide sequence of the invention, or that hybridize to a sequence of the invention are also encompassed.

DESCRIPTION OF FIGURES

FIG. 1 shows an alignment of the amino acid sequence of GRG32 (SEQ ID NO:1) with EPSP synthase sequences from *Xanthomonas axonopodis* (SEQ ID NO:6), two sequences from *Xanthomonas campestris* (SEQ ID NO:5 and SEQ ID NO:4), *Xanthomonas oryzae* (SEQ ID NO:3), three sequences from *Xylella fastidiosa* (SEQ ID NO:9, SEQ ID NO:7, and SEQ ID NO:8), *Agrobacterium tumefaciens* (SEQ ID NO:10), *Bacillus subtilis* (SEQ ID NO:11), *E. coli* (SEQ ID NO:12) and *Zea mays* (SEQ ID NO:13). The alignment shows the most highly conserved amino acid residues highlighted in black and highly conserved amino acid residues highlighted in gray

DETAILED DESCRIPTION

The present invention is drawn to compositions and methods for regulating herbicide resistance in organisms, particularly in plants or plant cells. The methods involve transforming organisms with a nucleotide sequence encoding a glyphosate resistance gene of the invention. In particular, a nucleotide sequence of the invention is useful for preparing plants that show increased tolerance to the herbicide glyphosate. Thus, transformed bacteria, plants, plant cells, plant tissues and seeds are provided. Compositions include nucleic acids and proteins relating to herbicide tolerance in microorganisms and plants as well as transformed bacteria, plants, plant tissues and seeds. More particularly, nucleotide sequences of the glyphosate resistance grg32 or syngrg32 gene and the amino acid sequence of the proteins encoded thereby are disclosed. The sequences find use in the construction of expression vectors for subsequent transformation into plants of interest, as probes for the isolation of other glyphosate resistance genes, as selectable markers, and the like. Thus, by "glyphosate resistance gene of the invention" is intended the nucleotide sequence set forth in SEQ ID NO:1 or 14 and fragments and variants thereof that encode a glyphosate resistance or tolerance polypeptide. Likewise, a "glyphosate resistance polypeptide of the invention" is a polypeptide having the amino acid sequence set forth in SEQ ID NO:2 and fragments and variants thereof that confer glyphosate resistance or tolerance to a host cell.

Plasmids containing the herbicide resistance nucleotide sequences of the invention were deposited in the permanent collection of the Agricultural Research Service Culture Collection, Northern Regional Research Laboratory (NRRL), 1815 North University Street, Peoria, Ill. 61604, United States of America, on Jun. 9, 2006, and assigned Accession No. B-30931. This deposit will be maintained under the terms of the Budapest Treaty on the International Recognition of the Deposit of Microorganisms for the Purposes of Patent Procedure. Access to these deposits will be available during the pendency of the application to the Commissioner of Patents and Trademarks and persons determined by the Commissioner to be entitled thereto upon request. Upon allowance of any claims in the application, the Applicants will make available to the public, pursuant to 37 C.F.R. §1.808, sample(s) of the deposit with the ATCC. This deposit was made merely as a convenience for those of skill in the art and is not an admission that a deposit is required under 35 U.S.C. §112.

By "glyphosate" is intended any herbicidal form of N-phosphonomethylglycine (including any salt thereof) and other forms that result in the production of the glyphosate anion in planta. An "herbicide resistance protein" or a protein resulting from expression of an "herbicide resistance-encoding nucleic acid molecule" includes proteins that confer upon a cell the ability to tolerate a higher concentration of an herbicide than cells that do not express the protein, or to tolerate a certain concentration of an herbicide for a longer period of time than cells that do not express the protein. A "glyphosate resistance protein" includes a protein that confers upon a cell the ability to tolerate a higher concentration of glyphosate than cells that do not express the protein, or to tolerate a certain concentration of glyphosate for a longer period of time than cells that do not express the protein. By "tolerate" or "tolerance" is intended either to survive, or to carry out essential cellular functions such as protein synthesis and respiration in a manner that is not readily discernable from untreated cells.

Isolated Nucleic Acid Molecules, and Variants and Fragments Thereof

One aspect of the invention pertains to isolated or recombinant nucleic acid molecules comprising nucleotide sequences encoding herbicide resistance proteins and polypeptides or biologically active portions thereof, as well as nucleic acid molecules sufficient for use as hybridization probes to identify herbicide resistance-encoding nucleic acids. As used herein, the term "nucleic acid molecule" is intended to include DNA molecules (e.g., cDNA, recombinant DNA, or genomic DNA) and RNA molecules (e.g., mRNA) and analogs of the DNA or RNA generated using nucleotide analogs. The nucleic acid molecules can be single-stranded or double-stranded, but preferably are double-stranded DNA.

Nucleotide sequences encoding the proteins of the present invention include the sequences set forth in SEQ ID NO:1 and 14, the herbicide resistance nucleotide sequence deposited in a bacterial host as Accession Nos. NRRL B-30931, and variants, fragments, and complements thereof. By "complement" is intended a nucleotide sequence that is sufficiently complementary to a given nucleotide sequence such that it can hybridize to the given nucleotide sequence to thereby form a stable duplex. The corresponding amino acid sequences for the herbicide resistance proteins encoded by these nucleotide sequences are set forth in SEQ ID NO:2. The invention also encompasses nucleic acid molecules comprising nucleotide sequences encoding partial-length herbicide resistance proteins, and complements thereof.

An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the invention, "isolated" when used to refer to nucleic acid molecules excludes isolated chromosomes. For example, in various embodiments, the isolated glyphosate resistance-encoding nucleic acid molecule can contain less than about 5 kb, 4 kb, 3 kb, 2 kb, 1 kb, 0.5 kb, or 0.1 kb of nucleotide sequence that naturally flanks the nucleic acid molecule in genomic DNA of the cell from which the nucleic acid is derived. An herbicide resistance protein that is substantially free of cellular material includes preparations of protein having less than about 30%, 20%, 10%, or 5% (by dry weight) of non-herbicide resistance protein (also referred to herein as a "contaminating protein").

Nucleic acid molecules that are fragments of these herbicide resistance-encoding nucleotide sequences are also encompassed by the present invention. By "fragment" is intended a portion of a nucleotide sequence encoding an herbicide resistance protein. A fragment of a nucleotide sequence may encode a biologically active portion of an herbicide resistance protein, or it may be a fragment that can be used as a hybridization probe or PCR primer using methods disclosed below. Nucleic acid molecules that are fragments of an herbicide resistance nucleotide sequence comprise at least about 15, 20, 50, 75, 100, 200, 300, 350, 400, 450, 500, 550, 600, 650, 700, 750, 800, 850, 900, 950, 1000, 1050, 1100, 1150, 1200, 1250, 1300, 1350 contiguous nucleotides, or up to the number of nucleotides present in a full-length herbicide resistance-encoding nucleotide sequence disclosed herein (for example, 1308 nucleotides for SEQ ID NO:1) depending upon the intended use. By "contiguous" nucleotides is intended nucleotide residues that are immediately adjacent to one another.

Fragments of the nucleotide sequences of the present invention generally will encode protein fragments that retain the biological activity of the full-length glyphosate resistance protein; i.e., herbicide-resistance activity. By "retains herbicide resistance activity" is intended that the fragment will have at least about 30%, at least about 50%, at least about 70%, or at least about 80% of the herbicide resistance activity of the full-length glyphosate resistance protein disclosed herein as SEQ ID NO:2. Methods for measuring herbicide resistance activity are well known in the art. See, for example, U.S. Pat. Nos. 4,535,060, and 5,188,642, each of which are herein incorporated by reference in their entirety.

A fragment of an herbicide resistance-encoding nucleotide sequence that encodes a biologically active portion of a protein of the invention will encode at least about 15, 25, 30, 50, 75, 100, 125, 150, 175, 200, 250, 300, 350, 400 contiguous amino acids, or up to the total number of amino acids present in a full-length herbicide resistance protein of the invention (for example, 435 amino acids for SEQ ID NO:2).

Preferred herbicide resistance proteins of the present invention are encoded by a nucleotide sequence sufficiently identical to the nucleotide sequence of SEQ ID NO:1 or 14. The term "sufficiently identical" is intended an amino acid or nucleotide sequence that has at least about 60% or 65% sequence identity, about 70% or 75% sequence identity, about 80% or 85% sequence identity, or about 90%, 91%, 92%, 93%, 94%, 95%, 96%, 97%, 98% or 99% sequence identity compared to a reference sequence using one of the alignment programs described herein using standard parameters. One of skill in the art will recognize that these values can be appropriately adjusted to determine corresponding identity of proteins encoded by two nucleotide sequences by taking into account codon degeneracy, amino acid similarity, reading frame positioning, and the like.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. A nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the BLASTN and BLASTX programs of Altschul et al. (1990) *J. Mol. Biol.* 215:403. BLAST nucleotide searches can be performed with the BLASTN program, score=100, wordlength=12, to obtain nucleotide sequences homologous to glyphosate-resistant nucleic acid molecules of the invention. BLAST protein searches can be performed with the BLASTX program, score=50, wordlength=3, to obtain amino acid sequences homologous to herbicide resistance protein molecules of the invention. To obtain gapped alignments for comparison purposes, Gapped BLAST can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., BLASTX and BLASTN) can be used. See www.ncbi.nlm.nih.gov.

Another non-limiting example of a mathematical algorithm utilized for the comparison of sequences is the ClustalW algorithm (Higgins et al. (1994) *Nucleic Acids Res.* 22:4673-4680). ClustalW compares sequences and aligns the entirety of the amino acid or DNA sequence, and thus can provide data about the sequence conservation of the entire amino acid sequence. The ClustalW algorithm is used in several commercially available DNA/amino acid analysis software packages, such as the ALIGNX module of the Vector NTI Program Suite (Invitrogen Corporation, Carlsbad, Calif.). After alignment of amino acid sequences with ClustalW, the percent amino acid identity can be assessed. A non-limiting example of a software program useful for analysis of ClustalW alignments is GENEDOC™. GENEDOC™ (Karl Nicholas) allows assessment of amino acid (or DNA) similarity and identity between multiple proteins. Another non-limiting example of a mathematical algorithm utilized for the comparison of sequences is the algorithm of Myers and Miller (1988) *CABIOS* 4:11-17. Such an algorithm is incorporated into the ALIGN program (version 2.0), which is part of the GCG sequence alignment software package (available from Accelrys, Inc., 9865 Scranton Rd., San Diego, Calif., USA). When utilizing the ALIGN program for comparing amino acid sequences, a PAM120 weight residue table, a gap length penalty of 12, and a gap penalty of 4 can be used.

Unless otherwise stated, GAP Version 10, which uses the algorithm of Needleman and Wunsch (1970) supra, will be used to determine sequence identity or similarity using the following parameters: % identity and % similarity for a nucleotide sequence using GAP Weight of 50 and Length Weight of 3, and the nwsgapdna.cmp scoring matrix; % identity or % similarity for an amino acid sequence using GAP weight of 8 and length weight of 2, and the BLOSUM62 scoring program. Equivalent programs may also be used. By "equivalent program" is intended any sequence comparison program that, for any two sequences in question, generates an alignment having identical nucleotide residue matches and an identical percent sequence identity when compared to the corresponding alignment generated by GAP Version 10.

The invention also encompasses variant nucleic acid molecules. "Variants" of the herbicide resistance-encoding nucleotide sequences include those sequences that encode an herbicide resistance protein disclosed herein but that differ conservatively because of the degeneracy of the genetic code, as well as those that are sufficiently identical as discussed above. Naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the herbicide resistance proteins disclosed in the present invention as discussed below. Variant proteins encompassed by the present invention are biologically active, that is they retain the desired biological activity of the native protein, that is, herbicide resistance activity. By "retains herbicide resistance activity" is intended that the variant will have at least about 30%, at least about 50%, at least about 70%, or at least about 80% of the herbicide resistance activity of the native protein. Methods for measuring herbicide resistance activity are well known in the art. See, for example, U.S. Pat. Nos. 4,535,060, and 5,188,642, each of which are herein incorporated by reference in their entirety.

The skilled artisan will further appreciate that changes can be introduced by mutation into the nucleotide sequences of the invention thereby leading to changes in the amino acid sequence of the encoded herbicide resistance protein, without altering the biological activity of the protein. Thus, variant isolated nucleic acid molecules can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, conservative amino acid substitutions may be made at one or more predicted, preferably nonessential amino acid residues. A "nonessential" amino acid residue is a residue that can be altered from the wild-type sequence of an herbicide resistance protein without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Amino acid substitutions may be made in nonconserved regions that retain function. In general, such substitutions would not be made for conserved amino acid residues, or for amino acid residues residing within a conserved motif, where such residues are essential for protein activity. However, one of skill in the art would understand that functional variants may have minor conserved or nonconserved alterations in the conserved residues. Examples of residues that are conserved and that may be essential for protein activity include, for example, residues that are identical between all proteins contained in the alignment of FIG. 2. Examples of residues that are conserved but that may allow conservative amino acid substitutions and still retain activity include, for example, residues that have only conservative substitutions between all proteins contained in the alignment of FIG. 2.

Lys-22, Arg-124, Asp-313, Arg-344, Arg-386, and Lys-411, are conserved residues of the EPSP synthase from *E. coli* (Schönbrunn et al. (2001) *Proc. Natl. Acad. Sci. USA* 98:1376-1380). Conserved residues important for EPSP synthase activity also include Arg-100, Asp-242, and Asp-384 (Selvapandiyan et al. (1995) *FEBS Letters* 374:253-256). Arg-27 binds to S3P (Shuttleworth et al. (1999) *Biochemistry* 38:296-302).

Alternatively, variant nucleotide sequences can be made by introducing mutations randomly along all or part of the coding sequence, such as by saturation mutagenesis, and the resultant mutants can be screened for ability to confer herbicide resistance activity to identify mutants that retain activity. Following mutagenesis, the encoded protein can be expressed recombinantly, and the activity of the protein can be determined using standard assay techniques.

Using methods such as PCR, hybridization, and the like, corresponding herbicide resistance sequences can be identified, such sequences having substantial identity to the sequences of the invention. See, for example, Sambrook J., and Russell, D. W. (2001) *Molecular Cloning: A Laboratory Manual*. (Cold Spring Harbor Laboratory Press, Cold Spring Harbor, N.Y.) and Innis, et al. (1990) *PCR Protocols: A Guide to Methods and Applications* (Academic Press, NY).

In a hybridization method, all or part of the herbicide resistance nucleotide sequence can be used to screen cDNA or genomic libraries. Methods for construction of such cDNA and genomic libraries are generally known in the art and are disclosed in Sambrook and Russell, 2001, supra. The so-called hybridization probes may be genomic DNA fragments, cDNA fragments, RNA fragments, or other oligonucleotides, and may be labeled with a detectable group such as $^{32}P$, or any other detectable marker, such as other radioisotopes, a fluorescent compound, an enzyme, or an enzyme co-factor. Probes for hybridization can be made by labeling synthetic oligonucleotides based on the known herbicide resistance-encoding nucleotide sequences disclosed herein. Degenerate primers designed on the basis of conserved nucleotides or amino acid residues in the nucleotide sequences or encoded amino acid sequences can additionally be used. The probe typically comprises a region of nucleotide sequence that hybridizes under stringent conditions to at least about 12, preferably about 25, at least about 50, 75, 100, 125, 150, 175, 200, 250, 300, 350, 400, 500, 600, 700, 800, 900, 1000, 1200, 1300 consecutive nucleotides of an herbicide resistance-encoding nucleotide sequence of the invention or a fragment or variant thereof. Methods for the preparation of probes for hybridization are generally known in the art and are disclosed in Sambrook and Russell, 2001, supra and Sambrook et al. (1989) *Molecular Cloning: A Laboratory Manual* (2d ed., Cold Spring Harbor Laboratory Press, Cold Spring Harbor, N.Y.), both of which are herein incorporated by reference.

For example, an entire herbicide resistance sequence disclosed herein, or one or more portions thereof, may be used as a probe capable of specifically hybridizing to corresponding herbicide resistance sequences and messenger RNAs. To achieve specific hybridization under a variety of conditions, such probes include sequences that are unique and are at least about 10 nucleotides in length, or at least about 20 nucleotides in length. Such probes may be used to amplify corresponding herbicide resistance sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Cold Spring Harbor, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6(log M)+0.41(% GC)−0.61(% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Cold Spring Harbor, N.Y.).

Isolated Proteins and Variants and Fragments Thereof

Herbicide resistance proteins are also encompassed within the present invention. By "herbicide resistance protein" is intended a protein having the amino acid sequence set forth in SEQ ID NO:2. Fragments, biologically active portions, and variants thereof are also provided, and may be used to practice the methods of the present invention.

"Fragments" or "biologically active portions" include polypeptide fragments comprising a portion of an amino acid sequence encoding an herbicide resistance protein as set forth SEQ ID NO:2, and that retains herbicide resistance activity. A biologically active portion of an herbicide resistance protein can be a polypeptide that is, for example, 10, 25, 50, 100 or more amino acids in length. Such biologically active portions can be prepared by recombinant techniques and evaluated for herbicide resistance activity. Methods for measuring herbicide resistance activity are well known in the art. See, for example, U.S. Pat. Nos. 4,535,060, and 5,188,642, each of which are herein incorporated by reference in their entirety. As used here, a fragment comprises at least 8 contiguous amino acids of SEQ ID NO:2. The invention encompasses other fragments, however, such as any fragment in the protein greater than about 10, 20, 30, 50, 100, 150, 200, 250, 300, 350, or 400 amino acids.

By "variants" is intended proteins or polypeptides having an amino acid sequence that is at least about 60%, 65%, about 70%, 75%, 80%, 85%, or 90%, 91%, 92%, 93%, 94%, 95%, 96%, 97%, 98% or 99% identical to the amino acid sequence of SEQ ID NO:2. Variants also include polypeptides encoded by a nucleic acid molecule that hybridizes to the nucleic acid molecule of SEQ ID NO:1 or 14, or a complement thereof, under stringent conditions. Variants include polypeptides that differ in amino acid sequence due to mutagenesis. Variant proteins encompassed by the present invention are biologically active, that is they continue to possess the desired biological activity of the native protein, that is, retaining herbicide resistance activity. Methods for measuring herbicide resistance activity are well known in the art. See, for example, U.S. Pat. Nos. 4,535,060, and 5,188,642, each of which are herein incorporated by reference in their entirety.

Bacterial genes, such as the grg32 gene of this invention, quite often possess multiple methionine initiation codons in proximity to the start of the open reading frame. Often, translation initiation at one or more of these start codons will lead to generation of a functional protein. These start codons can include ATG codons. However, bacteria such as Bacillus sp. also recognize the codon GTG as a start codon, and proteins that initiate translation at GTG codons contain a methionine at the first amino acid. Furthermore, it is not often determined a priori which of these codons are used naturally in the bacterium. Thus, it is understood that use of one of the alternate methionine codons may lead to generation of variants of grg32 that confer herbicide resistance. These herbicide resistance proteins are encompassed in the present invention and may be used in the methods of the present invention.

Antibodies to the polypeptides of the present invention, or to variants or fragments thereof, are also encompassed. Methods for producing antibodies are well known in the art (see, for example, Harlow and Lane (1988) *Antibodies: A Laboratory Manual*, Cold Spring Harbor Laboratory, Cold Spring Harbor, N.Y.; U.S. Pat. No. 4,196,265).

Altered or Improved Variants

It is recognized that DNA sequence of grg32 or syngrg32 may be altered by various methods, and that these alterations may result in DNA sequences encoding proteins with amino acid sequences different than that encoded by grg32. This protein may be altered in various ways including amino acid substitutions, deletions, truncations, and insertions of one or more amino acids of SEQ ID NO:1 or 14, including up to about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 100, about 105, about 110, about 115, about 120, about 125, about 130 or more amino acid substitutions, deletions or insertions.

Methods for such manipulations are generally known in the art. For example, amino acid sequence variants of the GRG proteins disclosed herein can be prepared by mutations in the DNA. This may also be accomplished by one of several forms of mutagenesis and/or in directed evolution. In some aspects, the changes encoded in the amino acid sequence will not substantially affect function of the protein. Such variants will possess the desired herbicide resistance activity. However, it is understood that the ability of GRG32 to confer herbicide resistance may be improved by one use of such techniques upon the compositions of this invention. For example, one may express grg32 in host cells that exhibit high rates of base misincorporation during DNA replication, such as XL-1 Red (Stratagene, La Jolla, Calif.). After propagation in such strains, one can isolate the DNA of the invention (for example by preparing plasmid DNA, or by amplifying by PCR and cloning the resulting PCR fragment into a vector), culture the grg mutations in a non-mutagenic strain, and identify mutated genes with improved resistance to an herbicide such as glyphosate, for example by growing cells in increasing concentrations of glyphosate and testing for clones that confer ability to tolerate increased concentrations of glyphosate.

Alternatively, alterations may be made to the protein sequence of many proteins at the amino or carboxy terminus without substantially affecting activity. This can include insertions, deletions, or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest, (2) introduce a binding domain, enzymatic activity, or epitope to facilitate either protein purification, protein detection, or other experimental uses known in the art, or, (3) target secretion or translation of a protein to a subcellular organelle, such as the periplasmic space of gram-negative bacteria, or the endoplasmic reticulum of eukaryotic cells, the latter of which often results in glycosylation of the protein.

Variant nucleotide and amino acid sequences of the present invention also encompass sequences derived from mutagenic and recombinogenic procedures such as DNA shuffling. With such a procedure, one or more different herbicide resistance protein coding regions can be used to create a new herbicide resistance protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the herbicide resistance gene of the invention and other known herbicide resistance genes to obtain a new gene coding for a protein with an improved property of interest, such as an increased glyphosate resistance activity. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

Transformation of Bacterial or Plant Cells

Provided herein are novel isolated genes that confer resistance to an herbicide. Also provided are amino acid sequences of the GRG proteins of the invention. The protein resulting from translation of this gene allows cells to function in the presence of concentrations of an herbicide that are otherwise toxic to cells including plant cells and bacterial cells. In one aspect of the invention, the grg32 or syngrg32 gene is useful as a marker to assess transformation of bacterial or plant cells. Methods for detecting the presence of a transgene in a plant, plant organ (e.g., leaves, stems, roots, etc.), seed, plant cell, propagule, embryo or progeny of the same are well known in the art.

By engineering the genes of the invention to be expressed from a promoter known to stimulate transcription in the organism to be tested and properly translated to generate an intact GRG peptide, and placing the cells in an otherwise toxic concentration of herbicide, one can identify cells that have been transformed with the DNA by virtue of their resistance to herbicide. By "promoter" is intended a nucleic acid sequence that functions to direct transcription of a downstream coding sequence. The promoter, together with other transcriptional and translational regulatory nucleic acid sequences, (also termed as "control sequences") are necessary for the expression of a DNA sequence of interest.

Transformation of bacterial cells is accomplished by one of several techniques known in the art, including but not limited to electroporation or chemical transformation (see, for example, Ausubel, ed. (1994) *Current Protocols in Molecular Biology*, John Wiley and Sons, Inc., Indianapolis, Ind.). Markers conferring resistance to toxic substances are useful in identifying transformed cells (having taken up and expressed the test DNA) from non-transformed cells (those not containing or not expressing the test DNA). In one aspect of the invention, the grg32 gene is useful as a marker to assess transformation of bacterial or plant cells.

Transformation of plant cells can be accomplished in similar fashion. By "plant" is intended whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells, pollen). "Transgenic plants" or "transformed plants" or "stably transformed" plants or cells or tissues refer to plants that have incorporated or integrated exogenous nucleic acid sequences or DNA fragments into the plant cell. By "stable transformation" is intended that the nucleotide construct introduced into a plant integrates into the genome of the plant and is capable of being inherited by progeny thereof.

The grg genes of the invention may be modified to obtain or enhance expression in plant cells. The herbicide resistance sequences of the invention may be provided in expression cassettes for expression in the plant of interest. "Plant expression cassette" includes DNA constructs, including recombinant DNA constructs, that are capable of resulting in the expression of a protein from an open reading frame in a plant cell. The cassette will include in the 5'-3' direction of transcription, a transcriptional initiation region (i.e., promoter, particularly a heterologous promoter) operably-linked to a DNA sequence of the invention, and/or a transcriptional and translational termination region (i.e., termination region) functional in plants. The cassette may additionally contain at least one additional gene to be cotransformed into the organism, such as a selectable marker gene. Alternatively, the additional gene(s) can be provided on multiple expression cassettes. Such an expression cassette is provided with a plurality of restriction sites for insertion of the herbicide resistance sequence to be under the transcriptional regulation of the regulatory regions.

The promoter may be native or analogous, or foreign or heterologous, to the plant host and/or to the DNA sequence of the invention. Additionally, the promoter may be the natural sequence or alternatively a synthetic sequence. Where the promoter is "native" or "homologous" to the plant host, it is intended that the promoter is found in the native plant into which the promoter is introduced. Where the promoter is "foreign" or "heterologous" to the DNA sequence of the invention, it is intended that the promoter is not the native or naturally occurring promoter for the operably linked DNA sequence of the invention. "Heterologous" generally refers to the nucleic acid sequences that are not endogenous to the cell or part of the native genome in which they are present, and have been added to the cell by infection, transfection, microinjection, electroporation, microprojection, or the like. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

Often, such constructs will also contain 5' and 3' untranslated regions. Such constructs may contain a "single sequence" or "leader sequence" to facilitate co-translational or post-translational transport of the peptide of interest to certain intracellular structures such as the chloroplast (or other plastid), endoplasmic reticulum, or Golgi apparatus, or to be secreted. For example, the gene can be engineered to contain a signal peptide to facilitate transfer of the peptide to the endoplasmic reticulum. By "signal sequence" is intended a sequence that is known or suspected to result in cotranslational or post-translational peptide transport across the cell membrane. In eukaryotes, this typically involves secretion into the Golgi apparatus, with some resulting glycosylation. By "leader sequence" is intended any sequence that when translated, results in an amino acid sequence sufficient to trigger co-translational transport of the peptide chain to a sub-cellular organelle. Thus, this includes leader sequences targeting transport and/or glycosylation by passage into the endoplasmic reticulum, passage to vacuoles, plastids including chloroplasts, mitochondria, and the like. It may also be preferable to engineer the plant expression cassette to contain an intron, such that mRNA processing of the intron is required for expression.

By "3' untranslated region" is intended a nucleotide sequence located downstream of a coding sequence. Polyadenylation signal sequences and other sequences encoding regulatory signals capable of affecting the addition of polyadenylic acid tracts to the 3' end of the mRNA precursor are 3' untranslated regions. By "5' untranslated region" is intended a nucleotide sequence located upstream of a coding sequence.

Other upstream or downstream untranslated elements include enhancers. Enhancers are nucleotide sequences that act to increase the expression of a promoter region. Enhancers are well known in the art and include, but are not limited to, the SV40 enhancer region and the 35S enhancer element.

The termination region may be native with the transcriptional initiation region, may be native with the herbicide resistance sequence of the present invention, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

In one aspect of the invention, synthetic DNA sequences are designed for a given polypeptide, such as the polypeptides of the invention. Expression of the open reading frame of the synthetic DNA sequence in a cell results in production of the polypeptide of the invention. Synthetic DNA sequences can be useful to simply remove unwanted restriction endonuclease sites, to facilitate DNA cloning strategies, to alter or remove any potential codon bias, to alter or improve GC content, to remove or alter alternate reading frames, and/or to alter or remove intron/exon splice recognition sites, polyadenylation sites, Shine-Delgarno sequences, unwanted promoter elements and the like that may be present in a native DNA sequence. It is also possible that synthetic DNA sequences may be utilized to introduce other improvements to a DNA sequence, such as introduction of an intron sequence, creation of a DNA sequence that in expressed as a protein fusion to organelle targeting sequences, such as chloroplast transit peptides, apoplast/vacuolar targeting peptides, or peptide sequences that result in retention of the resulting peptide in the endoplasmic reticulum. Synthetic genes can also be synthesized using host cell-preferred codons for improved expression, or may be synthesized using codons at a host-preferred codon usage frequency. See, for example, Campbell and Gowri (1990) *Plant Physiol.* 92:1-11; U.S. Pat. Nos. 6,320,100; 6,075,185; 5,380,831; and 5,436,391, U.S. Published Application Nos. 20040005600 and 20010003849, and Murray et al. (1989) *Nucleic Acids Res.* 17:477-498, herein incorporated by reference.

In one embodiment, the nucleic acids of interest are targeted to the chloroplast for expression. In this manner, where the nucleic acid of interest is not directly inserted into the chloroplast, the expression cassette will additionally contain a nucleic acid encoding a transit peptide to direct the gene product of interest to the chloroplasts. Such transit peptides are known in the art. See, for example, Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

The nucleic acids of interest to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

Typically this "plant expression cassette" will be inserted into a "plant transformation vector." By "transformation vector" is intended a DNA molecule that is necessary for efficient transformation of a cell. Such a molecule may consist of one or more expression cassettes, and may be organized into more than one "vector" DNA molecule. For example, binary vectors are plant transformation vectors that utilize two non-contiguous DNA vectors to encode all requisite cis- and trans-acting functions for transformation of plant cells (Hellens and Mullineaux (2000) *Trends in Plant Science* 5:446-451). "Vector" refers to a nucleic acid construct designed for transfer between different host cells. "Expression vector" refers to a vector that has the ability to incorporate, integrate and express heterologous DNA sequences or fragments in a foreign cell.

This plant transformation vector may be comprised of one or more DNA vectors needed for achieving plant transformation. For example, it is a common practice in the art to utilize plant transformation vectors that are comprised of more than one contiguous DNA segment. These vectors are often referred to in the art as "binary vectors." Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "gene of interest" (a gene engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the gene of interest are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as is understood in the art (Hellens and Mullineaux (2000) *Trends in Plant Science*, 5:446-451). Several types of *Agrobacterium* strains (e.g. LBA4404, GV3101, EHA101, EHA105, etc.) can be used for plant transformation. The second plasmid vector is not necessary for transforming the plants by other methods such as microprojection, microinjection, electroporation, polyethylene glycol, etc.

Plant Transformation

Methods of the invention involve introducing a nucleotide construct into a plant. By "introducing" is intended to present to the plant the nucleotide construct in such a manner that the construct gains access to the interior of a cell of the plant. The methods of the invention do not require that a particular method for introducing a nucleotide construct to a plant is used, only that the nucleotide construct gains access to the interior of at least one cell of the plant. Methods for introducing nucleotide constructs into plants are known in the art including, but not limited to, stable transformation methods, transient transformation methods, and virus-mediated methods.

In general, plant transformation methods involve transferring heterologous DNA into target plant cells (e.g. immature or mature embryos, suspension cultures, undifferentiated callus, protoplasts, etc.), followed by applying a maximum threshold level of appropriate selection (depending on the selectable marker gene and in this case "glyphosate") to recover the transformed plant cells from a group of untransformed cell mass. Explants are typically transferred to a fresh supply of the same medium and cultured routinely. Subsequently, the transformed cells are differentiated into shoots after placing on regeneration medium supplemented with a maximum threshold level of selecting agent (e.g. "glyphosate"). The shoots are then transferred to a selective rooting medium for recovering rooted shoot or plantlet. The transgenic plantlet then grow into mature plant and produce fertile seeds (e.g. Hiei et al. (1994) *The Plant Journal* 6:271-282; Ishida et al. (1996) *Nature Biotechnology* 14:745-750). Explants are typically transferred to a fresh supply of the same medium and cultured routinely. A general description of the techniques and methods for generating transgenic plants are found in Ayres and Park (1994) *Critical Reviews in Plant Science* 13:219-239 and Bommineni and Jauhar (1997) *Maydica* 42:107-120. Since the transformed material contains many cells, both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants. Molecular and biochemical methods can then be used to confirm the presence of the integrated heterologous gene of interest in the genome of transgenic plant.

Generation of transgenic plants may be performed by one of several methods, including but not limited to introduction of heterologous DNA by *Agrobacterium* into plant cells (*Agrobacterium*-mediated transformation), bombardment of plant cells with heterologous foreign DNA adhered to particles, and various other non-particle direct-mediated methods (e.g. Hiei et al. (1994) *The Plant Journal* 6:271-282; Ishida et al. (1996) *Nature Biotechnology* 14:745-750; Ayres and Park (1994) *Critical Reviews in Plant Science* 13:219-239; Bommineni and Jauhar (1997) *Maydica* 42:107-120) to transfer DNA.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-bome transgene by tissue-preferred expression of a nuclear-encoded and plastid-directed RNA polymerase. Such a system has been reported in McBride et al. (1994) *Proc. Natl. Acad. Sci. USA* 91:7301-7305.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

Plants

The present invention may be used for transformation of any plant species, including, but not limited to, monocots and dicots. Examples of plants of interest include, but are not limited to, corn (maize), sorghum, wheat, sunflower, tomato, crucifers, peppers, potato, cotton, rice, soybean, sugarbeet, sugarcane, tobacco, barley, and oilseed rape, *Brassica* sp., alfalfa, rye, millet, safflower, peanuts, sweet potato, cassava, coffee, coconut, pineapple, citrus trees, cocoa, tea, banana, avocado, fig, guava, mango, olive, papaya, cashew, macadamia, almond, oats, vegetables, ornamentals, and conifers.

Vegetables include, but are not limited to, tomatoes, lettuce, green beans, lima beans, peas, and members of the genus *Curcumis* such as cucumber, cantaloupe, and musk melon. Ornamentals include, but are not limited to, azalea, hydrangea, hibiscus, roses, tulips, daffodils, petunias, carnation, poinsettia, and chrysanthemum. Preferably, plants of the present invention are crop plants (for example, maize, sorghum, wheat, sunflower, tomato, crucifers, peppers, potato, cotton, rice, soybean, sugarbeet, sugarcane, tobacco, barley, oilseed rape, etc.).

This invention is particularly suitable for any member of the monocot plant family including, but not limited to, maize, rice, barley, oats, wheat, sorghum, rye, sugarcane, pineapple, yams, onion, banana, coconut, and dates.

Evaluation of Plant Transformation

Following introduction of heterologous foreign DNA into plant cells, the transformation or integration of heterologous gene in the plant genome is confirmed by various methods such as analysis of nucleic acids, proteins and metabolites associated with the integrated gene.

PCR analysis is a rapid method to screen transformed cells, tissue or shoots for the presence of incorporated gene at the earlier stage before transplanting into the soil (Sambrook and Russell (2001) *Molecular Cloning: A Laboratory Manual*, Cold Spring Harbor Laboratory Press, Cold Spring Harbor, N.Y.). PCR is carried out using oligonucleotide primers specific to the gene of interest or *Agrobacterium* vector background, etc.

Plant transformation may be confirmed by Southern blot analysis of genomic DNA (Sambrook and Russell, 2001, supra). In general, total DNA is extracted from the transformant, digested with appropriate restriction enzymes, fractionated in an agarose gel and transferred to a nitrocellulose or nylon membrane. The membrane or "blot" is then probed with, for example, radiolabeled $^{32}$P target DNA fragments to confirm the integration of the introduced gene in the plant genome according to standard techniques (Sambrook and Russell, 2001, supra).

In Northern analysis, RNA is isolated from specific tissues of transformant, fractionated in a formaldehyde agarose gel, blotted onto a nylon filter according to standard procedures that are routinely used in the art (Sambrook and Russell, 2001, supra). Expression of RNA encoded by grg32 is then tested by hybridizing the filter to a radioactive probe derived from a polynucleotide of the invention, by methods known in the art (Sambrook and Russell, 2001, supra)

Western blot and biochemical assays and the like may be carried out on the transgenic plants to determine the presence of protein encoded by the herbicide resistance gene by standard procedures (Sambrook and Russell, 2001, supra) using antibodies that bind to one or more epitopes present on the herbicide resistance protein.

Methods for Increasing Plant Yield

Methods for increasing plant yield are provided. The methods comprise introducing into a plant or plant cell a polynucleotide comprising a grg sequence disclosed herein. As defined herein, the "yield" of the plant refers to the quality and/or quantity of biomass produced by the plant. By "biomass" is intended any measured plant product. An increase in biomass production is any improvement in the yield of the measured plant product. Increasing plant yield has several commercial applications. For example, increasing plant leaf biomass may increase the yield of leafy vegetables for human or animal consumption. Additionally, increasing leaf biomass can be used to increase production of plant-derived pharmaceutical or industrial products. An increase in yield can comprise any statistically significant increase including, but not limited to, at least a 1% increase, at least a 3% increase, at least a 5% increase, at least a 10% increase, at least a 20% increase, at least a 30%, at least a 50%, at least a 70%, at least a 100% or a greater increase.

In specific methods, the plant is treated with an effective concentration of an herbicide, where the herbicide application results in enhanced plant yield. By "effective concentration" is intended the concentration which allows the increased yield in the plant. Such effective concentrations for herbicides of interest are generally known in the art. The herbicide may be applied either pre- or post emergence in accordance with usual techniques for herbicide application to fields comprising crops which have been rendered resistant to the herbicide by heterologous expression of a grg gene of the invention.

Methods for conferring herbicide resistance in a plant or plant part are also provided. In such methods, a grg polynucleotide disclosed herein is introduced into the plant, wherein expression of the polynucleotide results in glyphosate tolerance or resistance. Plants produced via this method can be treated with an effective concentration of an herbicide and display an increased tolerance to the herbicide. An "effective concentration" of an herbicide in this application is an amount sufficient to slow or stop the growth of plants or plant parts that are not naturally resistant or rendered resistant to the herbicide.

Methods of Controlling Weeds in a Field

Methods for selectively controlling weeds in a field containing a plant are also provided. In one embodiment, the plant seeds or plants are glyphosate resistant as a result of a grg polynucleotide disclosed herein being inserted into the plant seed or plant. In specific methods, the plant is treated with an effective concentration of an herbicide, where the herbicide application results in a selective control of weeds or other untransformed plants. By "effective concentration" is intended the concentration which controls the growth or spread of weeds or other untransformed plants without significantly affecting the glyphosate-resistant plant or plant seed. Such effective concentrations for herbicides of interest are generally known in the art. The herbicide may be applied either pre- or post emergence in accordance with usual techniques for herbicide application to fields comprising plants or plant seeds which have been rendered resistant to the herbicide.

The following examples are offered by way of illustration and not by way of limitation.

EXPERIMENTAL

Example 1

Isolation of Glyphosate Resistant EPSP Synthases

Strains capable of growth in presence of glyphosate were isolated by plating samples of soil on HEPES Mineral Salts Medium (HMSM) containing glyphosate as the sole source of phosphorus. Since HMSM contains no aromatic amino acids, a strain must be resistant to glyphosate in order to grow on this media.

Two grams of soil were suspended in approximately 10 ml of water, vortexed for 15 seconds and permitted to settle for 15 minutes. A 10 µl loopful of this suspension was added to 3 ml of HMSM supplemented with 10 mM glyphosate (pH 7.0). HMSM contains (per liter): 10 g glucose, 2 g $NH_4SO_4$, 9.53 g HEPES, 1.0 ml 0.8 M $MgSO_4$, 1.0 ml 0.1 M $CaCl_2$, 1.0 ml Trace Elements Solution (In 100 ml of 1000× solution: 0.1 g $FeSO_4.7H_2O$, 0.5 mg $CuSO_4.5H_2O$, 1.0 mg $H_3BO_3$, 1.0 mg $MnSO_4.5H_2O$, 7.0 mg $ZnSO_4.7H_2O$, 1.0 mg $MoO_3$, 4.0 g KCl). The culture was grown in a shaker incubator for four days at 28° C. and then 20 µl was used to inoculate 2.5 ml of fresh HMSM containing 10 mM glyphosate as the only phosphorus source. After two days, 20 µl was used to inoculate another fresh 2.5 ml culture. After 5 days, 20 µl was used to inoculate a fresh 2.5 ml culture. After sufficient growth, the culture was plated onto solid media by streaking a 1 μl loop onto the surface of agar plate containing HMSM agar containing 100 mM glyphosate as the sole phosphorus source and stored at 28° C. The culture was then replated for isolation. Strain ATX21556 was selected due to its ability to grow in the presence of high glyphosate concentrations.

Example 2

Cloning of Glyphosate-Resistant EPSP Synthases

Genomic DNA was extracted from strain ATX21556 and the resulting DNA was partially digested with restriction enzyme Sau3A 1 to yield DNA fragments approximately 5 kilobases in size. These DNA molecules were size selected on agarose gels, purified, and ligated into LAMBDA ZAP® vector arms pre-digested with BamH I. The ligated arms were then packaged into phage particles, and phage titers determined as known in the art. The resulting libraries were amplified by methods known in the art to generate a library titer of between $3\times10^7$ and $3\times10^8$ PFU/mL. *E. coli* (XL1 Blue MRF') was then co-transfected with phage from an amplified library as well as M13 helper phage to allow mass excision of the library in the form of an infectious, circular ssDNA as known in the art (Short et al. (1988) *Nucleic Acids Research* 16:7583-7600). After centrifugation of the co-infected cells, the phage-containing supernatant was heated to 65-70° C. for 15-20 minutes to incapacitate any residual lambda phage particles. Dilutions of the resulting ssDNA plasmid library were transfected into a fresh culture of competent *E. coli* XL-Blue MRF'(aroA) cells (XL1 Blue MRF'). The resulting transfected cells were plated onto M63 plates containing kanamycin, 0.1 mM IPTG and either 0 mM, 20 mM or 50 mM glyphosate.

The *E. coli* XL-Blue MRF'(aroA) used for the transfection expresses the F-pilus, and also contains a deletion of the aroA gene encoding the endogenous *E. coli* EPSP synthase enzyme. This strain is also referred to as herein as ΔaroA. This ΔaroA strain is unable to grow on minimal media lacking aromatic amino acids, unless complemented by a functional EPSP synthase. Since glyphosate is a potent inhibitor of typical, glyphosate-sensitive EPSP synthases, such as type I EPSP synthases, transfected clones expressing a non-glyphosate resistant EPSP synthase would be able to grown on M63 plates lacking glyphosate, but would be unable to grow on M63 containing either 20 mM or 50 mM glyphosate. In order to grow on M63 plates containing 20 mM or 50 mM glyphosate, the cells must contain a plasmid that expresses an EPSP synthase that is both (1) capable of complementing the ΔaroA mutation of these cells, and (2) resistant to glyphosate. Thus, this screening method allows identification of clones containing glyphosate-resistant EPSP synthases.

Colonies growing on 20 mM or 50 mM glyphosate were picked and their plasmids analyzed by restriction digest to identify plasmids with shared restriction patterns. Individual plasmids were sequenced by methods known in the art, with preference given to plasmids that conferred resistance to 50 mM glyphosate.

Using this approach, as sometimes modified for each library as known and appreciated in the art, library clones containing EPSP synthase genes were identified.

Example 3

DNA and Protein Sequences of EPSP Synthases

The DNA sequence of the glyphosate-resistant EPSP synthase was determined by methods well known in the art. The DNA sequence of grg32 is provided herein as SEQ ID NO:1. The predicted translation product of grg32 (GRG32) is provided herein as SEQ ID NO:2. Clone pAX1946 containing the grg32 EPSP synthase gene was deposited at NRRL on Jun. 9, 2006 and assigned Accession No. NRRL B-30931. A synthetic sequence encoding GRG32 was designed and is herein referred to as syngrg32 (SEQ ID NO:14).

A search of public protein databases with the amino acid sequence of GRG32 shows that this protein is related to the EPSP synthases from *Xanthomonas* sp., including the EPSP synthases from *Xanthomonas oryzae* pv. *oryzae* (SEQ ID NO:3, GENBANK® Accession No. BAE 69021) and from *Xanthomonas campestris* pv. *vesicatoria* str. 85-10 (SEQ ID NO:4, GENBANK® Accession No. YP_363422.1), *Xanthomonas campestris* pv. *Campestris* str. ATCC 33913 (SEQ ID NO:5, GENBANK® Accession No. AAM40886), *Xanthomonas axonopodis* pv. *citri* str. 306 (SEQ ID NO:6; GENBANK® Accession No. AAM36518.1), and to a lesser extent Xylella sp including *Xylella fastidiosa* Ann-I (SEQ ID NO:7; GENBANK® Accession No. ZP00680509.1) and *Xylella fastidiosa* Temecula1 (SEQ ID NO:8; GENBANK® Accession No. NP779554.1)

TABLE 1

Amino acid identity of GRG32 with EPSP synthases

| EPSP synthase | SEQ ID NO: | Identity with GRG32 |
|---|---|---|
| *Xanthomonas oryzae* pv. *oryzae* | 3 | 83% |
| *Xanthomonas campestris* pv. *vesicatoria* | 4 | 82% |
| *Xanthomonas campestris* pv. *campestris* | 5 | 82% |
| *Xanthomonas axonopodis* pv. *citri* str. 306 | 6 | 81% |
| *Xylella fastidiosa* Ann-1 | 7 | 74% |
| *Xylella fastidiosa* Temecula1 | 8 | 72% |
| *Xylella fastidiosa* 9a5c | 9 | 71% |
| CP4-*Agrobacterium tumefaciens* | 10 | 43% |
| *B. subtilis* | 11 | 43% |
| *E. coli* | 12 | 25% |
| *Zea mays* | 13 | 25% |

Example 4

Cloning of grg32 into an *E. Coil* Expression Vector

The grg32 gene contained in pAX1946 was sub-cloned into the *E. coli* expression vector pRSF1b (Invitrogen). Resulting clones were confirmed by DNA sequencing, and used to induce expression of grg32 in *E. coli*. The expressed His-tagged protein was then purified as known in the art.

Example 5

Glyphosate Resistance of EPSP Synthases

The pRSF1b clones were plated onto M63+ plates containing antibiotic and either 0 mM or 50 mM glyphosate. Growth was scored after two days growth at 37° C. GRG32 was observed to confer resistance to 50 mM glyphosate in *E. coli* cells (Table 2).

TABLE 2

Glyphosate screen

| EPSPS | Clone in pRSF1B | Growth on 50 mM glyphosate |
|---|---|---|
| Vector | — | — |
| GRG32 | pAX1950 | +++ |

Example 6

Engineering grg32 or svngrg32 for Plant Transformation

The open reading frame (ORF) for grg32 or syngrg32 gene is amplified by PCR from a full-length cDNA template. Hind III restriction sites are added to each end of the ORF during PCR. Additionally, the nucleotide sequence ACC is added immediately 5' to the start codon of the gene to increase translational efficiency (Kozak (1987) *Nucleic Acids Research* 15:8125-8148; Joshi (1987) *Nucleic Acids Research* 15:6643-6653). The PCR product is cloned and sequenced, using techniques well known in the art, to ensure that no mutations are introduced during PCR. The plasmid containing the grg32 PCR product is digested with, for example, Hind III and the fragment containing the intact ORF is isolated.

One may generate similar constructs that contain a chloroplast targeting sequence linked to the polynucleotide of the invention by methods known in the art.

A DNA fragment containing the EPSP synthase (and either containing or not containing a chloroplast targeting sequence) is cloned into a plasmid, for example at the Hind III site of pAX200. pAX200 is a plant expression vector containing the rice actin promoter (McElroy et al. (1991) *Molec. Gen. Genet.* 231:150-160), and the PinII terminator (An et al. (1989) *The Plant Cell* 1:115-122). The promoter-gene-terminator fragment (or the promoter-leader-gene-terminator fragment) from this intermediate plasmid is subcloned into a plasmid such as pSB11 (Japan Tobacco, Inc.) to form a final plasmid, referred to herein as, for example, pSB11GRG32. pSB11GRG32 is organized such that the DNA fragment containing, for example, the promoter-grg32-terminator construct (or the promoter-leader-grg32-terminator construct) may be excised by appropriate restriction enzymes and also used for transformation into plants, for example, by aerosol beam injection. The structure of pSB11GRG32 is verified by restriction digest and gel electrophoresis, as well as by sequencing across the various cloning junctions. The same methods can be used to generate a final plasmid for each of the grg genes described herein.

The plasmid is mobilized into *Agrobacterium tumefaciens* strain LBA4404 which also harbors the plasmid pSB1 (Japan Tobacco, Inc.), using triparental mating procedures well known in the art, and plating on media containing antibiotic. Plasmid pSB11GRG32 carries spectinomycin resistance but is a narrow host range plasmid and cannot replicate in *Agrobacterium*. Antibiotic resistant colonies arise when pSB11GRG32 integrates into the broad host range plasmid pSB1 through homologous recombination. The resulting cointegrate product is verified by Southern hybridization. The *Agrobacterium* strain harboring the cointegrate can be used to transform maize, for example, by the PureIntro method (Japan Tobacco).

Example 7

Transformation grg32 or syngrg32 into Plant Cells

Maize ears are best collected 8-12 days after pollination. Embryos are isolated from the ears, and those embryos 0.8-1.5 mm in size are preferred for use in transformation. Embryos are plated scutellum side-up on a suitable incubation media, such as DN62A5S media (3.98 g/L N6 Salts; 1 mL/L (of 1000× Stock) N6 Vitamins; 800 mg/L L-Asparagine; 100 mg/L Myo-inositol; 1.4 g/L L-Proline; 100 mg/L Casamino acids; 50 g/L sucrose; 1 mL/L (of 1 mg/mL Stock) 2,4-D). However, media and salts other than DN62A5S are suitable and are known in the art. Embryos are incubated overnight at 25° C. in the dark. However, it is not necessary per se to incubate the embryos overnight.

The resulting explants are transferred to mesh squares (30-40 per plate), transferred onto osmotic media for about 30-45 minutes, then transferred to a beaming plate (see, for example, PCT Publication No. WO/0138514 and U.S. Pat. No. 5,240,842).

DNA constructs designed to express the GRG proteins of the present invention in plant cells are accelerated into plant tissue using an aerosol beam accelerator, using conditions essentially as described in PCT Publication No. WO/0138514. After beaming, embryos are incubated for about 30 min on osmotic media, and placed onto incubation media overnight at 25° C. in the dark. To avoid unduly damaging beamed explants, they are incubated for at least 24 hours prior to transfer to recovery media. Embryos are then spread onto recovery period media, for about 5 days, 25° C. in the dark, then transferred to a selection media. Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated by methods known in the art. The resulting shoots are allowed to root on rooting media, and the resulting plants are transferred to nursery pots and propagated as transgenic plants.

Materials

TABLE 3

DN62A5S Media

| Components | Per Liter | Source |
|---|---|---|
| Chu's N6 Basal Salt Mixture (Prod. No. C 416) | 3.98 g/L | Phytotechnology Labs |
| Chu's N6 Vitamin Solution (Prod. No. C 149) | 1 mL/L (of 1000× Stock) | Phytotechnology Labs |
| L-Asparagine | 800 mg/L | Phytotechnology Labs |
| Myo-inositol | 100 mg/L | Sigma |
| L-Proline | 1.4 g/L | Phytotechnology Labs |
| Casamino acids | 100 mg/L | Fisher Scientific |
| Sucrose | 50 g/L | Phytotechnology Labs |
| 2,4-D (Prod. No. D-7299) | 1 mL/L (of 1 mg/mL Stock) | Sigma |

The pH of the solution is adjusted to pH 5.8 with 1N KOH/1N KCl, Gelrite (Sigma) is added at a concentration up to 3 g/L, and the media is autoclaved. After cooling to 50° C., 2 ml/L of a 5 mg/ml stock solution of silver nitrate (Phytotechnology Labs) is added.

Example 8

Transformation of grg32 or syngrg32 into Maize Plant Cells by *Agrobacterium*-Mediated Transformation Ears are best collected 8-12 days after pollination. Embryos are isolated from the ears, and those embryos 0.8-1.5 mm in size are preferred for use in transformation. Embryos are plated scutellum side-up on a suitable incubation media, and incubated overnight at 25° C. in the dark. However, it is not necessary per se to incubate the embryos overnight. Embryos are contacted with an *Agrobacterium* strain containing the appropriate vectors for Ti plasmid mediated transfer for about 5-10 min, and then plated onto co-cultivation media for about 3 days (25° C. in the dark). After co-cultivation, explants are transferred to recovery period media for about five days (at 25° C. in the dark). Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated as known in the art. The resulting shoots are allowed to root on rooting media, and the resulting plants are transferred to nursery pots and propagated as transgenic plants.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

---

That which is claimed:

1. An isolated or recombinant nucleic acid molecule comprising a nucleotide sequence selected from the group consisting of:
   a) the nucleotide sequence of SEQ ID NO:1 or 14, or a complement thereof;
   b) the herbicide resistance nucleotide sequence of the DNA insert of the plasmid deposited as Accession No. NRRL B-30931, or a complement thereof;
   c) a nucleotide sequence that encodes a polypeptide comprising the amino acid sequence of SEQ ID NO:2; and,
   d) a nucleotide sequence encoding a polypeptide having at least 95% amino acid sequence identity to the amino acid sequence of SEQ ID NO:2, wherein said polypeptide has herbicide resistance activity.

2. The isolated or recombinant nucleic acid molecule of claim 1, wherein said nucleotide sequence is a synthetic sequence that has been designed for expression in a plant.

3. A vector comprising the nucleic acid molecule of claim 1.

4. The vector of claim 3, further comprising a nucleic acid molecule encoding a heterologous polypeptide.

5. The isolated or recombinant nucleic acid molecule of claim 1, wherein said nucleotide sequence is operably linked to a promoter capable of directing expression of a coding sequence in a plant.

6. A host cell that contains the nucleic acid molecule of claim 5.

7. The host cell of claim 6 that is a bacterial host cell.

8. The host cell of claim 6 that is a plant cell.

9. A transgenic plant comprising the host cell of claim 8.

10. The plant of claim 9, wherein said plant is selected from the group consisting of maize, sorghum, wheat, sunflower, tomato, crucifers, peppers, potato, cotton, rice, soybean, sugarbeet, sugarcane, tobacco, barley, and oilseed rape.

11. A seed comprising the nucleic acid molecule of claim 5.

12. A method for producing a polypeptide with herbicide resistance activity, comprising culturing the host cell of claim 6 under conditions in which a nucleic acid molecule encoding the polypeptide is expressed, said polypeptide being selected from the group consisting of:
   a) a polypeptide comprising the amino acid sequence of SEQ ID NO:2;
   b) a polypeptide encoded by the nucleic acid sequence of SEQ ID NO:1 or 14;
   c) a polypeptide comprising an amino acid sequence having at least 95% sequence identity to the amino acid sequence of SEQ ID NO:2, wherein said polypeptide has herbicide resistance activity; and
   d) a polypeptide that is encoded by the herbicide resistance nucleotide sequence of the DNA insert of the plasmid deposited as Accession No. NRRL B-30931.

13. A method for conferring resistance to an herbicide in a plant, said method comprising transforming said plant with a DNA construct, said construct comprising a promoter that drives expression in a plant cell operably linked with a nucleotide sequence, and regenerating a transformed plant, wherein said nucleotide sequence is selected from the group consisting of:
   a) the nucleotide sequence of SEQ ID NO:1 or 14;
   b) the herbicide resistance nucleotide sequence of the DNA insert of the plasmid deposited as Accession No. NRRL B-30931;
   c) a nucleotide sequence that encodes a polypeptide comprising the amino acid sequence of SEQ ID NO:2; and, d) a nucleotide sequence encoding a polypeptide having at least 95% amino acid sequence identity to the amino acid sequence of SEQ ID NO:2, wherein said polypeptide has herbicide resistance activity.

14. A plant having stably incorporated into its genome a DNA construct comprising a nucleotide sequence that encodes a protein having herbicide resistance activity, wherein said nucleotide sequence is selected from the group consisting of:
  a) a nucleotide sequence of SEQ ID NO:1 or 14;
  b) a nucleotide sequence encoding a polypeptide comprising the amino acid sequence of SEQ ID NO:2;
  c) a nucleotide sequence encoding a polypeptide having at least 95% amino acid sequence identity to the amino acid sequence of SEQ ID NO:2, wherein said polypeptide has herbicide resistance activity; and,
  d) the herbicide resistance nucleotide sequence of the DNA insert of the plasmid deposited as Accession No. NRRL B-30931; wherein said nucleotide sequence is operably linked to a promoter that drives expression of a coding sequence in a plant cell.

15. The plant of claim 14, wherein said plant is a plant cell.

* * * * *

SEQUENCE LISTING

```
<160> NUMBER OF SEQ ID NOS: 14

<210> SEQ ID NO 1
<211> LENGTH: 1308
<212> TYPE: DNA
<213> ORGANISM: Unknown
<220> FEATURE:
<223> OTHER INFORMATION: Isolated from soil sample
<220> FEATURE:
<221> NAME/KEY: CDS
<222> LOCATION: (1)...(1308)

<400> SEQUENCE: 1 atg acc gct tcc gct tcc tgg acc gcc cgc aag ggc cag ccc ctg cag      48
Met Thr Ala Ser Ala Ser Trp Thr Ala Arg Lys Gly Gln Pro Leu Gln
 1               5                   10                  15 ggc agc ctg acc att ccc ggc gac aag tcg gtc tcg cac cgt gcg gtg      96
Gly Ser Leu Thr Ile Pro Gly Asp Lys Ser Val Ser His Arg Ala Val
             20                  25                  30 atg ttc gct gca ctg gcc gat ggc gtt tcg cac atc gac ggt ttc ctg     144
Met Phe Ala Ala Leu Ala Asp Gly Val Ser His Ile Asp Gly Phe Leu
         35                  40                  45 gaa ggc gag gac acc cgc gcc acc gcc gcg atc ttc tcg cag atg ggc     192
Glu Gly Glu Asp Thr Arg Ala Thr Ala Ala Ile Phe Ser Gln Met Gly
     50                  55                  60 gtg cgc att gaa acc ccg tcg ccg tcg cag cgc atc gtc cac ggc gtg     240
Val Arg Ile Glu Thr Pro Ser Pro Ser Gln Arg Ile Val His Gly Val
 65                  70                  75                  80 ggc gtg gat ggt ctg cag gca ccg gcc ggc ccg ctg gac tgc ggc aac     288
Gly Val Asp Gly Leu Gln Ala Pro Ala Gly Pro Leu Asp Cys Gly Asn
                 85                  90                  95 gcc ggc acc ggc atg cgc ctg ctg gcc ggc ctc gcc gcg cag ccg          336
Ala Gly Thr Gly Met Arg Leu Leu Ala Gly Leu Leu Ala Ala Gln Pro
            100                 105                 110 ttc gat gca gtg atg gtg ggc gat gaa tcg ctg tcg cgc cgt ccc atg     384
Phe Asp Ala Val Met Val Gly Asp Glu Ser Leu Ser Arg Arg Pro Met
        115                 120                 125 cgc cgg gtg acc ggc ccg ctg gcg cag atg ggc gcg aag atc gac acc     432
Arg Arg Val Thr Gly Pro Leu Ala Gln Met Gly Ala Lys Ile Asp Thr
    130                 135                 140 gag gcc gac ggc acc ccg ccg ctg cgc gtg cat ggc ggc cag ccg ctg     480
```

```
Glu Ala Asp Gly Thr Pro Pro Leu Arg Val His Gly Gln Pro Leu
145                 150                 155                 160 cac ggc atc gac ttc gcc tcg ccg gtg gcc agc gcg cag gtc aaa tcg    528
His Gly Ile Asp Phe Ala Ser Pro Val Ala Ser Ala Gln Val Lys Ser
                165                 170                 175 gcc gtg ctg ctg gcc ggc ctg tat gcg cag ggc gag acc tcc gtg acc    576
Ala Val Leu Leu Ala Gly Leu Tyr Ala Gln Gly Glu Thr Ser Val Thr
            180                 185                 190 gaa ccg cac ccg acc cgc gac tac agc gaa cgc atg ctg cgt gcg ttc    624
Glu Pro His Pro Thr Arg Asp Tyr Ser Glu Arg Met Leu Arg Ala Phe
        195                 200                 205 ggt gtc gag att gaa ttt tct ccc ggc aag gcc cgc ctg cgt ggc ggc    672
Gly Val Glu Ile Glu Phe Ser Pro Gly Lys Ala Arg Leu Arg Gly Gly
    210                 215                 220 cag cgc ctg cgc gcc acc gac atc gcc gtg ccg gcc gac ttc tcc tct    720
Gln Arg Leu Arg Ala Thr Asp Ile Ala Val Pro Ala Asp Phe Ser Ser
225                 230                 235                 240 gcg gcg ttc ttc ctc gtc gcc gcc agc atc att ccc ggt tcg gca ctc    768
Ala Ala Phe Phe Leu Val Ala Ala Ser Ile Ile Pro Gly Ser Ala Leu
                245                 250                 255 acc ctg cgc cag gtc ggc ctc aac ccg cgc cgc acc ggc ctg ctc gcc    816
Thr Leu Arg Gln Val Gly Leu Asn Pro Arg Arg Thr Gly Leu Leu Ala
            260                 265                 270 gcg ctg cga ctg atg ggc gcg gat atc cgc gaa gag aac cat gca gag    864
Ala Leu Arg Leu Met Gly Ala Asp Ile Arg Glu Glu Asn His Ala Glu
        275                 280                 285 cag ggc ggg gaa gcc gta gca gac ctg gtg gtc cgc cat gca ccg ctt    912
Gln Gly Gly Glu Ala Val Ala Asp Leu Val Val Arg His Ala Pro Leu
    290                 295                 300 cac ggt gcc gag att ccc gag gcg ctg gtg ccg gac atg atc gac gag    960
His Gly Ala Glu Ile Pro Glu Ala Leu Val Pro Asp Met Ile Asp Glu
305                 310                 315                 320 ttc ccg gcc ctg ttc gtt gcc gcg gcc gct gca cag ggc aac acc atc    1008
Phe Pro Ala Leu Phe Val Ala Ala Ala Ala Gln Gly Asn Thr Ile
                325                 330                 335 gtg cgc ggg gcg gcc gaa ctg cga gtc aag gaa tcc gac cgc ctc gcg    1056
Val Arg Gly Ala Ala Glu Leu Arg Val Lys Glu Ser Asp Arg Leu Ala
            340                 345                 350 gcc atg gcc acc ggc ctg cgc agc ctc ggc gta cag gtg gat gaa acc    1104
Ala Met Ala Thr Gly Leu Arg Ser Leu Gly Val Gln Val Asp Glu Thr
        355                 360                 365 gaa gac ggc gcc acg atc cac ggt ggg cat gag ctg ggc agc ggc acc    1152
Glu Asp Gly Ala Thr Ile His Gly Gly His Glu Leu Gly Ser Gly Thr
    370                 375                 380 atc gaa agc cac ggc gac cac cgc atc gcc atg gcc ttc gcc atc gcc    1200
Ile Glu Ser His Gly Asp His Arg Ile Ala Met Ala Phe Ala Ile Ala
385                 390                 395                 400 ggc cag ctc agc agc ggc gag gtg cgc atc aac gac atc gcc aac gtc    1248
Gly Gln Leu Ser Ser Gly Glu Val Arg Ile Asn Asp Ile Ala Asn Val
                405                 410                 415 gcc acc tcg ttc ccc aac ttc gac ggc atc gcc cgc acc gcc ggc ttc    1296
Ala Thr Ser Phe Pro Asn Phe Asp Gly Ile Ala Arg Thr Ala Gly Phe
            420                 425                 430 aac ctc ggg taa                                                     1308
Asn Leu Gly  *
            435

<210> SEQ ID NO 2
<211> LENGTH: 435
<212> TYPE: PRT
<213> ORGANISM: Unknown
```

<220> FEATURE:
<223> OTHER INFORMATION: Isolated from soil sample

<400> SEQUENCE: 2

```
Met Thr Ala Ser Ala Ser Trp Thr Ala Arg Lys Gly Gln Pro Leu Gln
  1               5                  10                  15

Gly Ser Leu Thr Ile Pro Gly Asp Lys Ser Val Ser His Arg Ala Val
             20                  25                  30

Met Phe Ala Ala Leu Ala Asp Gly Val Ser His Ile Asp Gly Phe Leu
         35                  40                  45

Glu Gly Glu Asp Thr Arg Ala Thr Ala Ala Ile Phe Ser Gln Met Gly
     50                  55                  60

Val Arg Ile Glu Thr Pro Ser Pro Ser Gln Arg Ile Val His Gly Val
 65                  70                  75                  80

Gly Val Asp Gly Leu Gln Ala Pro Ala Gly Pro Leu Asp Cys Gly Asn
                 85                  90                  95

Ala Gly Thr Gly Met Arg Leu Leu Ala Gly Leu Leu Ala Ala Gln Pro
            100                 105                 110

Phe Asp Ala Val Met Val Gly Asp Glu Ser Leu Ser Arg Arg Pro Met
        115                 120                 125

Arg Arg Val Thr Gly Pro Leu Ala Gln Met Gly Ala Lys Ile Asp Thr
130                 135                 140

Glu Ala Asp Gly Thr Pro Pro Leu Arg Val His Gly Gly Gln Pro Leu
145                 150                 155                 160

His Gly Ile Asp Phe Ala Ser Pro Val Ala Ser Ala Gln Val Lys Ser
                165                 170                 175

Ala Val Leu Leu Ala Gly Leu Tyr Ala Gln Gly Glu Thr Ser Val Thr
            180                 185                 190

Glu Pro His Pro Thr Arg Asp Tyr Ser Glu Arg Met Leu Arg Ala Phe
        195                 200                 205

Gly Val Glu Ile Glu Phe Ser Pro Gly Lys Ala Arg Leu Arg Gly Gly
    210                 215                 220

Gln Arg Leu Arg Ala Thr Asp Ile Ala Val Pro Ala Asp Phe Ser Ser
225                 230                 235                 240

Ala Ala Phe Phe Leu Val Ala Ala Ser Ile Ile Pro Gly Ser Ala Leu
                245                 250                 255

Thr Leu Arg Gln Val Gly Leu Asn Pro Arg Arg Thr Gly Leu Leu Ala
            260                 265                 270

Ala Leu Arg Leu Met Gly Ala Asp Ile Arg Glu Glu Asn His Ala Glu
        275                 280                 285

Gln Gly Gly Glu Ala Val Ala Asp Leu Val Val Arg His Ala Pro Leu
    290                 295                 300

His Gly Ala Glu Ile Pro Glu Ala Leu Val Pro Asp Met Ile Asp Glu
305                 310                 315                 320

Phe Pro Ala Leu Phe Val Ala Ala Ala Gln Gly Asn Thr Ile
                325                 330                 335

Val Arg Gly Ala Ala Glu Leu Arg Val Lys Glu Ser Asp Arg Leu Ala
            340                 345                 350

Ala Met Ala Thr Gly Leu Arg Ser Leu Gly Val Gln Val Asp Glu Thr
        355                 360                 365

Glu Asp Gly Ala Thr Ile His Gly Gly His Glu Leu Gly Ser Gly Thr
    370                 375                 380

Ile Glu Ser His Gly Asp His Arg Ile Ala Met Ala Phe Ala Ile Ala
385                 390                 395                 400
```

Gly Gln Leu Ser Ser Gly Glu Val Arg Ile Asn Asp Ile Ala Asn Val
            405                 410                 415

Ala Thr Ser Phe Pro Asn Phe Asp Gly Ile Ala Arg Thr Ala Gly Phe
            420                 425                 430

Asn Leu Gly
        435

<210> SEQ ID NO 3
<211> LENGTH: 440
<212> TYPE: PRT
<213> ORGANISM: Xanthomonas oryzae pv. oryzae MAFF 311018

<400> SEQUENCE: 3

Met Ser Ser Asn Thr His His Trp Ile Ala Arg Ar

```
Val Val Thr Gly Ala Ala Glu Leu Arg Val Lys Glu Ser Asp Arg Leu
            340                 345                 350

Ala Ala Met Ala Thr Gly Leu Arg Thr Leu Gly Val Gln Val Asp Glu
            355                 360                 365

Thr Pro Asp Gly Ala Thr Ile His Gly Gly Ser Ile Gly Ser Gly Val
            370                 375                 380

Ile Glu Ser His Gly Asp His Arg Ile Ala Met Ala Phe Ala Ile Ala
385                 390                 395                 400

Gly Gln Leu Ser Ser Gly Ser Val Arg Val Asn Asp Val Ala Asn Val
                405                 410                 415

Ala Thr Ser Phe Pro Gly Phe Asp Thr Leu Ala Gln Ala Gly Ala Phe
            420                 425                 430

Gly Leu Glu Ala Ala Glu Ser Gly
            435                 440

<210> SEQ ID NO 4
<211> LENGTH: 440
<212> TYPE: PRT
<213> ORGANISM: Xanthomonas campestris pv. vesicatoria str. 85-10

<400> SEQUENCE: 4

Met Ser Ser Ser Thr His His Trp Ile Ala Arg Arg Gly Thr Ala Leu
1               5                   10                  15

Gln Gly Ser Le

```
Ala Ala Leu Arg Leu Met Gly Ala Glu Ile Ser Glu Glu Asn His Ala
            275                 280                 285

Glu His Gly Gly Glu Pro Val Ala Asp Leu Arg Val Arg Tyr Ala Pro
    290                 295                 300

Leu Arg Gly Ala Gln Ile Pro Glu Ala Leu Val Pro Asp Met Ile Asp
305                 310                 315                 320

Glu Phe Pro Ala Leu Phe Val Ala Ala Ala Ala Ser Gly Gln Thr
                325                 330                 335

Val Val Thr Gly Ala Ala Glu Leu Arg Val Lys Glu Ser Asp Arg Leu
                340                 345                 350

Ala Ala Met Ala Thr Gly Leu Arg Thr Leu Gly Val Gln Val Asp Glu
            355                 360                 365

Thr Pro Asp Gly Ala Thr Ile His Gly Ser Ile Gly Ser Gly Val
    370                 375                 380

Ile Glu Ser His Gly Asp His Arg Ile Ala Met Ala Phe Ala Ile Ala
385                 390                 395                 400

Gly Gln Leu Ser Thr Gly Gln Val Gln Val Asn Asp Val Ala Asn Val
                405                 410                 415

Ala Thr Ser Phe Pro Gly Phe Asp Thr Leu Ala Gln Gly Ala Gly Phe
            420                 425                 430

Gly Leu Glu Thr Ala Gly Arg Arg
            435                 440

<210> SEQ ID NO 5
<211> LENGTH: 438
<212> TYPE: PRT
<213> ORGANISM: Xanthomonas campestris pv. campestris str. ATCC 33

<400> SEQUENCE: 5

Met Ser Asn Ser Thr Gln His Trp Ile Ala Gln Arg Gly Thr Ala Leu
1               5                   10                  15

Gln Gly Ser Leu Thr Ile Pro Gly Asp Lys Ser Val Ser His Arg Ala
            20                  25                  30

Val Met Phe Ala Ala Leu Ala Asp Gly Ile Ser Lys Ile Asp Gly

```
Phe Gly Val Glu Ile Ala Phe Ser Pro Gly Gln Ala Arg Leu Arg Gly
        210                 215                 220

Gly Gln Arg Leu Arg Ala Thr Asp Ile Ala Val Pro Ala Asp Phe Ser
225                 230                 235                 240

Ser Ala Ala Phe Phe Ile Val Ala Ala Ser Ile Ile Pro Gly Ser Gly
                    245                 250                 255

Val Thr Leu Arg Ala Val Gly Leu Asn Pro Arg Arg Thr Gly Leu Leu
                260                 265                 270

Ala Ala Leu Arg Leu Met Gly Ala Asp Ile Val Glu Asp Asn His Ala
            275                 280                 285

Glu His Gly Gly Glu Pro Val Ala Asp Leu Arg Val Arg Tyr Ala Pro
        290                 295                 300

Leu Arg Gly Ala Gln Ile Pro Glu Ala Leu Val Pro Asp Met Ile Asp
305                 310                 315                 320

Glu Phe Pro Ala Leu Phe Val Ala Ala Ala Ala Arg Gly Asp Thr
                    325                 330                 335

Val Val Ser Gly Ala Ala Glu Leu Arg Val Lys Glu Ser Asp Arg Leu
                340                 345                 350

Ala Ala Met Ala Thr Gly Leu Arg Ala Leu Gly Ile Val Val Asp Glu
            355                 360                 365

Thr Pro Asp Gly Ala Thr Ile His Gly Gly Thr Leu Gly Ser Gly Val
        370                 375                 380

Ile Glu Ser His Gly Asp His Arg Ile Ala Met Ala Phe Ala Ile Ala
385                 390                 395                 400

Gly Gln Leu Ser Thr Gly Thr Val Gln Val Asn Asp Val Ala Asn Val
                405                 410                 415

Ala Thr Ser Phe Pro Gly Phe Asp Ser Leu Ala Gln Gly Ala Gly Phe
                420                 425                 430

Gly Leu Ser Ala Arg Pro
            435

<210> SEQ ID NO 6
<211> LENGTH: 440
<212> TYPE: PRT
<213> ORGANISM: Xanthomonas axonopodis pv. citri str. 306

<400> SEQUENCE: 6

Met Ser Ser Ser Thr His His Trp Ile Ala Arg Arg Gly Thr Ala Leu
1               5                   10                  15

Gln Gly Ser Leu Ala Ile Pro Gly Asp Lys Ser Val Ser His Arg Ala
                20                  25                  30

Val Met Phe Ala Ala Leu Ala Asp Gly Val Ser Gln Ile Asp Gly Phe
            35                  40                  45

Leu Glu Gly Glu Asp Thr Arg Ser Thr Ala Ala Ile Phe Ala Lys Leu
50                  55                  60

Gly Val Arg Ile Glu Thr Pro Ser Ala Ser Gln Arg Ile Val His Gly
65                  70                  75                  80

Val Gly Val Asp Gly Leu Gln Pro Pro Thr Glu Val Leu Asp Cys Gly
                85                  90                  95

Asn Ala Gly Thr Gly Met Arg Leu Leu Ala Gly Leu Leu Ala Ala Gln
            100                 105                 110

Arg Phe Asp Ser Val Leu Val Gly Asp Ala Ser Leu Ser Lys Arg Pro
        115                 120                 125

Met Arg Arg Val Thr Gly Pro Leu Ala Gln Met Gly Ala Arg Ile Glu
130                 135                 140
```

```
Thr Gln Asp Asp Gly Thr Pro Pro Leu His Val Arg Gly Gly Gln Ala
145                 150                 155                 160

Leu His Gly Ile Asp Phe Val Ser Pro Val Ala Ser Ala Gln Val Lys
            165                 170                 175

Ser Ala Val Leu Leu Ala Gly Leu Tyr Ala Gln Gly Glu Thr Ser Val
        180                 185                 190

Thr Glu Pro His Pro Thr Arg Asp Tyr Thr Glu Arg Met Leu Ser Ala
    195                 200                 205

Phe Gly Val Glu Ile Asp Phe Ser Pro Gly Lys Ala Arg Leu Arg Gly
210                 215                 220

Gly Gln Arg Leu Arg Ala Thr Asp Ile Ala Val Pro Ala Asp Phe Ser
225                 230                 235                 240

Ser Ala Ala Phe Phe Ile Val Ala Ala Ser Val Val Pro Gly Ser Glu
                245                 250                 255

Val Val Leu Arg Ala Val Gly Leu Asn Pro Arg Arg Thr Gly Leu Leu
                260                 265                 270

Ala Ala Leu Arg Leu Met Gly Ala Asp Ile Gly Glu Glu Asn His Ala
                275                 280                 285

Glu His Gly Gly Glu Pro Val Ala Asp Leu His Val Arg Tyr Ala Pro
290                 295                 300

Leu Arg Gly Ala Gln Ile Pro Glu Ala Leu Val Pro Asp Met Ile Asp
305                 310                 315                 320

Glu Phe Pro Ala Leu Phe Val Ala Ala Ala Ala Ser Gly Gln Thr
                325                 330                 335

Val Val Thr Gly Ala Ala Glu Leu Arg Val Lys Glu Ser Asp Arg Leu
                340                 345                 350

Ala Ala Met Ala Thr Gly Leu Arg Thr Leu Gly Ile Gln Val Asp Glu
                355                 360                 365

Thr Pro Asp Gly Ala Thr Ile His Gly Gly Ser Ile Gly Ser Gly Val
                370                 375                 380

Ile Glu Ser His Gly Asp His Arg Ile Ala Met Ala Phe Ala Ile Ala
385                 390                 395                 400

Gly Gln Leu Ser Met Gly Gln Val Gln Val Asn Asp Val Ala Asn Val
                405                 410                 415

Ala Thr Ser Phe Pro Gly Phe Asp Thr Leu Ala Gln Asp Val Gly Phe
                420                 425                 430

Gly Leu Glu Thr Ala Gly His Arg
            435                 440

<210> SEQ ID NO 7
<211> LENGTH: 442
<212> TYPE: PRT
<213> ORGANISM: Xylella fastidiosa Ann-1

<400> SEQUENCE: 7

Met Ser His Arg Thr His Tyr Tyr Trp Ile Ala His Gln Gly Thr Pro
 1               5                  10                  15

Leu His Gly Val Leu Ser Ile Pro Gly Asp Lys Ser Ile Ser His Arg
                20                  25                  30

Ala Val Met Phe Ala Ala Leu Ala Asp Gly Thr Ser Arg Ile Asp Gly
            35                  40                  45

Phe Leu Glu Ala Glu Asp Thr Arg Ser Thr Ala Ala Ile Leu Ala Arg
    50                  55                  60

Leu Gly Val Arg Ile Glu Thr Pro Ser Ser Thr Gln Arg Ile Val His
65                  70                  75                  80
```

Gly Val Gly Val Asp Gly Phe Gln Ala Ser Asp Ile Ala Leu Asp Cys
            85                  90                  95

Gly Asn Ala Gly Thr Gly Met Arg Leu Leu Ala Gly Leu Leu Val Ala
            100                 105                 110

Gln Pro Phe Asp Ser Val Leu Val Gly Asp Ala Ser Leu Ser Lys Arg
            115                 120                 125

Pro Met Arg Arg Val Thr Asp Pro Leu Ser Gln Met Gly Ala Arg Ile
130                 135                 140

Asp Thr Ser Asp Asp Gly Thr Pro Pro Leu Arg Ile Tyr Gly Gly Gln
145                 150                 155                 160

Leu Leu Arg Gly Ile Asp Phe Ile Ser Pro Val Ala Ser Ala Gln Ile
            165                 170                 175

Lys Ser Ala Val Leu Leu Ala Gly Leu Tyr Ala Arg Asn Glu Thr Val
            180                 185                 190

Val Arg Glu Pro His Pro Thr Arg Asp Tyr Thr Glu Arg Met Leu Thr
            195                 200                 205

Ala Phe Gly Val Asp Ile Asp Val Ser Thr Gly Cys Ala Arg Leu Arg
            210                 215                 220

Gly Gly Gln Arg Leu Cys Ala Thr Asn Ile Thr Ile Pro Ala Asp Phe
225                 230                 235                 240

Ser Ser Ala Ala Phe Tyr Leu Val Ala Ala Ser Val Ile Pro Gly Ser
            245                 250                 255

Asp Ile Thr Leu Arg Ala Val Gly Leu Asn Pro Arg Arg Ile Gly Leu
            260                 265                 270

Leu Thr Val Leu Arg Leu Met Gly Ala Asp Ile Val Glu Ser Asn Cys
            275                 280                 285

His Glu Gln Gly Gly Glu Pro Val Ala Asp Leu Arg Val Arg Tyr Ala
            290                 295                 300

Pro Leu Gln Gly Thr Arg Val Pro Glu Asp Leu Val Pro Asp Met Ile
305                 310                 315                 320

Asp Glu Phe Pro Val Leu Phe Ile Ala Ala Ala Ala Glu Gly Gln
            325                 330                 335

Thr Val Val Ser Gly Ala Ala Glu Leu Arg Val Lys Glu Ser Asp Arg
            340                 345                 350

Leu Ala Ala Met Val Thr Gly Leu Arg Val Leu Gly Val Gln Val Asp
            355                 360                 365

Glu Thr Ala Asp Gly Ala Thr Ile His Gly Pro Ile Gly His Gly
            370                 375                 380

Thr Ile Asn Ser His Gly Asp His Arg Ile Ala Met Ala Phe Ser Ile
385                 390                 395                 400

Ala Gly Gln Leu Ser Val Ser Thr Val Arg Ile Glu Asp Val Ala Asn
            405                 410                 415

Val Ala Thr Ser Phe Pro Asn Tyr Glu Thr Leu Ala Arg Ser Ala Gly
            420                 425                 430

Phe Gly Leu Glu Val Tyr Cys Asp Pro Ala
            435                 440

<210> SEQ ID NO 8
<211> LENGTH: 454
<212> TYPE: PRT
<213> ORGANISM: Xylella fastidiosa Temecula1

<400> SEQUENCE: 8

Met Tyr Cys Arg Arg Ser Gln Leu Lys Lys Pro Ser Met Ser His Arg
1               5                   10                  15

```
Thr His Tyr Tyr Trp Ile Ala His Gln Gly Thr Pro Leu His Gly Val
            20                  25                  30

Leu Ser Ile Pro Gly Asp Lys Ser Ile Ser His Arg Ala Val Met Phe
        35                  40                  45

Ala Ala Leu Ala Asp Gly Thr Ser Arg Ile Asp Gly Phe Leu Glu Ala
50                      55                  60

Glu Asp Thr Arg Ser Thr Ala Ala Ile Leu Ala Arg Leu Gly Val Arg
65                  70                  75                  80

Ile Glu Thr Pro Ser Phe Thr Gln Arg Ile Val His Gly Val Gly Val
                85                  90                  95

Asp Gly Leu Gln Ala Ser Asp Ile Ala Leu Asp Cys Gly Asn Ala Gly
                100                 105                 110

Thr Gly Met Arg Leu Leu Ala Gly Leu Leu Val Ala Gln Pro Phe Asp
            115                 120                 125

Ser Val Leu Val Gly Asp Ala Ser Leu Ser Lys Arg Pro Met Arg Arg
        130                 135                 140

Val Thr Asp Pro Leu Ser Gln Met Gly Ala Arg Ile Asp Thr Ser Asp
145                 150                 155                 160

Asp Gly Thr Pro Pro Leu Arg Ile Tyr Gly Gly Gln Leu Leu Arg Gly
                165                 170                 175

Ile Asp Phe Ile Ser Pro Val Ala Ser Ala Gln Ile Lys Ser Ala Val
                180                 185                 190

Leu Leu Ala Gly Leu Tyr Ala Arg Asn Glu Thr Val Arg Glu Pro
        195                 200                 205

His Pro Thr Arg Asp Tyr Thr Glu Arg Met Leu Thr Ala Phe Gly Val
        210                 215                 220

Asp Ile Asp Val Ser Thr Gly Cys Val Arg Leu Arg Gly Gly Gln Arg
225                 230                 235                 240

Leu Cys Ala Thr Asn Ile Thr Ile Pro Ala Asp Phe Ser Ser Ala Ala
                245                 250                 255

Phe Tyr Leu Val Ala Ala Ser Val Ile Pro Gly Ser Asp Ile Thr Leu
            260                 265                 270

Arg Ala Val Gly Leu Asn Pro Arg Arg Ile Gly Leu Leu Thr Val Leu
        275                 280                 285

Arg Leu Met Gly Ala Asp Ile Val Glu Ser Asn Arg His Glu Gln Gly
        290                 295                 300

Gly Glu Pro Val Ala Asp Leu Arg Val Arg Tyr Ala Ser Leu Gln Gly
305                 310                 315                 320

Thr Arg Val Pro Glu Asp Leu Val Pro Asp Met Ile Asp Glu Phe Pro
                325                 330                 335

Ala Leu Phe Val Ala Ala Ala Ala Glu Gly Gln Thr Val Val Ser
            340                 345                 350

Gly Ala Ala Glu Leu Arg Val Lys Glu Ser Asp Arg Leu Ala Ala Met
        355                 360                 365

Val Thr Gly Leu Arg Val Leu Gly Val Gln Val Asp Glu Thr Ala Asp
        370                 375                 380

Gly Ala Thr Ile His Gly Gly Pro Ile Gly His Gly Thr Ile Asn Ser
385                 390                 395                 400

His Gly Asp His Arg Ile Ala Met Ala Phe Ser Ile Ala Gly Gln Leu
                405                 410                 415

Ser Val Ser Thr Val Arg Ile Glu Asp Val Ala Asn Val Ala Thr Ser
            420                 425                 430

Phe Pro Asp Tyr Glu Thr Leu Ala Arg Ser Ala Gly Phe Gly Leu Glu
        435                 440                 445
```

Val Tyr Cys Asp Pro Ala
    450

<210> SEQ ID NO 9
<211> LENGTH: 454
<212> TYPE: PRT
<213> ORGANISM: Xylella fastidiosa 9a5c

<400> SEQUENCE: 9

Met Tyr Cys Arg Arg Ser His Leu Lys Lys Pro Ser Met Ser His Arg
  1               5                  10                  15

Thr His Asp Tyr Trp Ile Ala His Gln Gly Thr Pro Leu His Gly Val
             20                  25                  30

Leu Ser Ile Pro Gly Asp Lys Ser Ile Ser His Arg Ala Val Met Phe
         35                  40                  45

Ala Ala Leu Ala Asp Gly Thr Ser Arg Ile Asp Gly Phe Leu Glu Ala
     50                  55                  60

Glu Asp Thr Cys Ser Thr Ala Glu Ile Leu Ala Arg Leu Gly Val Arg
 65                  70                  75                  80

Ile Glu Thr Pro Leu Ser Thr Gln Arg Ile Val His Gly Val Gly Val
                 85                  90                  95

Asp Gly Leu Gln Ala Ser His Ile Pro Leu Asp Cys Gly Asn Ala Gly
            100                 105                 110

Thr Gly Met Arg Leu Leu Ala Gly Leu Leu Val Ala Gln Pro Phe Asp
        115                 120                 125

Ser Val Leu Val Gly Asp Ala Ser Leu Ser Lys Arg Pro Met Arg Arg
    130                 135                 140

Val Thr Asp Pro Leu Ser Gln Met Gly Ala Arg Ile Asp Thr Ser Asp
145                 150                 155                 160

Asp Gly Thr Pro Pro Leu Arg Ile Tyr Gly Gly Gln Leu Leu His Gly
                165                 170                 175

Ile Asp Phe Ile Ser Pro Val Ala Ser Ala Gln Ile Lys Ser Ala Val
            180                 185                 190

Leu Leu Ala Gly Leu Tyr Ala Arg Asn Glu Thr Val Val Arg Glu Pro
        195                 200                 205

His Pro Thr Arg Asp Tyr Thr Glu Arg Met Leu Thr Ala Phe Gly Val
    210                 215                 220

Asp Ile Asp Val Ser Thr Gly Cys Ala Arg Leu Arg Gly Gly Gln Arg
225                 230                 235                 240

Leu Cys Ala Thr Asp Ile Thr Ile Pro Ala Asp Phe Ser Ser Ala Ala
                245                 250                 255

Phe Tyr Leu Val Ala Ala Ser Val Ile Pro Gly Ser Asp Ile Thr Leu
            260                 265                 270

Arg Ala Val Gly Leu Asn Pro Arg Arg Ile Gly Leu Leu Thr Val Leu
        275                 280                 285

Arg Leu Met Gly Ala Asn Ile Val Glu Ser Asn Arg His Glu Gln Gly
    290                 295                 300

Gly Glu Pro Val Val Asp Leu Arg Val Arg Tyr Ala Pro Leu Gln Gly
305                 310                 315                 320

Thr Arg Val Pro Glu Asp Leu Val Ala Asp Met Ile Asp Glu Phe Pro
                325                 330                 335

Ala Leu Phe Val Ala Ala Ala Ala Glu Gly Gln Thr Val Val Ser
            340                 345                 350

Gly Ala Ala Glu Leu Arg Val Lys Glu Ser Asp Arg Leu Ala Ala Met
        355                 360                 365

```
Val Thr Gly Leu Arg Val Leu Gly Val Gln Val Asp Glu Thr Ala Asp
        370                 375                 380

Gly Ala Thr Ile His Gly Gly Pro Ile Gly His Gly Thr Ile Asn Ser
385                 390                 395                 400

His Gly Asp His Arg Ile Ala Met Ala Phe Ser Ile Ala Gly Gln Leu
                405                 410                 415

Ser Val Ser Thr Val Arg Ile Glu Asp Val Ala Asn Val Ala Thr Ser
                420                 425                 430

Phe Pro Asp Tyr Glu Thr Leu Ala Arg Ser Ala Gly Phe Gly Leu Glu
                435                 440                 445

Val Tyr Cys Asp Pro Ala
                450

<210> SEQ ID NO 10
<211> LENGTH: 455
<212> TYPE: PRT
<213> ORGANISM: Agrobacterium tumefaciens strain CP4

<400> SEQUENCE: 10

Met Ser His Gly Ala Ser Ser Arg Pro Ala Thr Ala Arg Lys Ser Ser
  1               5                  10                  15

Gly Leu Ser Gly Thr Val Arg Ile Pro Gly Asp Lys Ser Ile Ser His
                20                  25                  30

Arg Ser Phe Met Phe Gly Gly Leu Ala Ser Gly Glu Thr Arg Ile Thr
            35                  40                  45

Gly Leu Leu Glu Gly Glu Asp Val Ile Asn Thr Gly Lys Ala Met Gln
        50                  55                  60

Ala Met Gly Ala Arg Ile Arg Lys Glu Gly Asp Thr Trp Ile Ile Asp
65                  70                  75                  80

Gly Val Gly Asn Gly Gly Leu Leu Ala Pro Glu Ala Pro Leu Asp Phe
                85                  90                  95

Gly Asn Ala Ala Thr Gly Cys Arg Leu Thr Met Gly Leu Val Gly Val
            100                 105                 110

Tyr Asp Phe Asp Ser Thr Phe Ile Gly Asp Ala Ser Leu Thr Lys Arg
        115                 120                 125

Pro Met Gly Arg Val Leu Asn Pro Leu Arg Glu Met Gly Val Gln Val
130                 135                 140

Lys Ser Glu Asp Gly Asp Arg Leu Pro Val Thr Leu Arg Gly Pro Lys
145                 150                 155                 160

Thr Pro Thr Pro Ile Thr Tyr Arg Val Pro Met Ala Ser Ala Gln Val
                165                 170                 175

Lys Ser Ala Val Leu Leu Ala Gly Leu Asn Thr Pro Gly Ile Thr Thr
            180                 185                 190

Val Ile Glu Pro Ile Met Thr Arg Asp His Thr Glu Lys Met Leu Gln
        195                 200                 205

Gly Phe Gly Ala Asn Leu Thr Val Glu Thr Asp Ala Asp Gly Val Arg
    210                 215                 220

Thr Ile Arg Leu Glu Gly Arg Gly Lys Leu Thr Gly Gln Val Ile Asp
225                 230                 235                 240

Val Pro Gly Asp Pro Ser Ser Thr Ala Phe Pro Leu Val Ala Ala Leu
                245                 250                 255

Leu Val Pro Gly Ser Asp Val Thr Ile Leu Asn Val Leu Met Asn Pro
            260                 265                 270

Thr Arg Thr Gly Leu Ile Leu Thr Leu Gln Glu Met Gly Ala Asp Ile
        275                 280                 285
```

```
Glu Val Ile Asn Pro Arg Leu Ala Gly Gly Glu Asp Val Ala Asp Leu
    290                 295                 300

Arg Val Arg Ser Ser Thr Leu Lys Gly Val Thr Val Pro Glu Asp Arg
305                 310                 315                 320

Ala Pro Ser Met Ile Asp Glu Tyr Pro Ile Leu Ala Val Ala Ala Ala
                325                 330                 335

Phe Ala Glu Gly Ala Thr Val Met Asn Gly Leu Glu Glu Leu Arg Val
            340                 345                 350

Lys Glu Ser Asp Arg Leu Ser Ala Val Ala Asn Gly Leu Lys Leu Asn
        355                 360                 365

Gly Val Asp Cys Asp Glu Gly Glu Thr Ser Leu Val Val Arg Gly Arg
    370                 375                 380

Pro Asp Gly Lys Gly Leu Gly Asn Ala Ser Gly Ala Ala Val Ala Thr
385                 390                 395                 400

His Leu Asp His Arg Ile Ala Met Ser Phe Leu Val Met Gly Leu Val
                405                 410                 415

Ser Glu Asn Pro Val Thr Val Asp Asp Ala Thr Met Ile Ala Thr Ser
            420                 425                 430

Phe Pro Glu Phe Met Asp Leu Met Ala Gly Leu Gly Ala Lys Ile Glu
        435                 440                 445

Leu Ser Asp Thr Lys Ala Ala
    450                 455

<210> SEQ ID NO 11
<211> LENGTH: 428
<212> TYPE: PRT
<213> ORGANISM: Bacillus subtilis

<400> SEQUENCE: 11

Met Lys Arg Asp Lys Val Gln Thr Leu His Gly Glu Ile His Ile Pro
1               5                   10                  15

Gly Asp Lys Ser Ile Ser His Arg Ser Val Met Phe Gly Ala Leu Ala
                20                  25                  30

Ala Gly Thr Thr Thr Val Lys Asn Phe Leu Pro Gly Ala Asp Cys Leu
            35                  40                  45

Ser Thr Ile Asp Cys Phe Arg Lys Met Gly Val His Ile Glu Gln Ser
        50                  55                  60

Ser Ser Asp Val Val Ile His Gly Lys Gly Ile Asp Ala Leu Lys Glu
65                  70                  75                  80

Pro Glu Ser Leu Leu Asp Val Gly Asn Ser Gly Thr Thr Ile Arg Leu
                85                  90                  95

Met Leu Gly Ile Leu Ala Gly Arg Pro Phe Tyr Ser Ala Val Ala Gly
            100                 105                 110

Asp Glu Ser Ile Ala Lys Arg Pro Met Lys Arg Val Thr Glu Pro Leu
        115                 120                 125

Lys Lys Met Gly Ala Lys Ile Asp Gly Arg Ala Gly Gly Glu Phe Thr
    130                 135                 140

Pro Leu Ser Val Ser Gly Ala Ser Leu Lys Gly Ile Asp Tyr Val Ser
145                 150                 155                 160

Pro Val Ala Ser Ala Gln Ile Lys Ser Ala Val Leu Leu Ala Gly Leu
                165                 170                 175

Gln Ala Glu Gly Thr Thr Thr Val Thr Glu Pro His Lys Ser Arg Asp
            180                 185                 190

His Thr Glu Arg Met Leu Ser Ala Phe Gly Val Lys Leu Ser Glu Asp
        195                 200                 205
```

```
Gln Thr Ser Val Ser Ile Ala Gly Gly Gln Lys Leu Thr Ala Ala Asp
    210                 215                 220

Ile Phe Val Pro Gly Asp Ile Ser Ser Ala Ala Phe Phe Leu Ala Ala
225                 230                 235                 240

Gly Ala Met Val Pro Asn Ser Arg Ile Val Leu Lys Asn Val Gly Leu
                245                 250                 255

Asn Pro Thr Arg Thr Gly Ile Ile Asp Val Leu Gln Asn Met Gly Ala
            260                 265                 270

Lys Leu Glu Ile Lys Pro Ser Ala Asp Ser Gly Ala Glu Pro Tyr Gly
        275                 280                 285

Asp Leu Ile Ile Glu Thr Ser Ser Leu Lys Ala Val Glu Ile Gly Gly
    290                 295                 300

Asp Ile Ile Pro Arg Leu Ile Asp Glu Ile Pro Ile Ile Ala Leu Leu
305                 310                 315                 320

Ala Thr Gln Ala Glu Gly Thr Thr Val Ile Lys Asp Ala Ala Glu Leu
                325                 330                 335

Lys Val Lys Glu Thr Asn Arg Ile Asp Thr Val Val Ser Glu Leu Arg
            340                 345                 350

Lys Leu Gly Ala Glu Ile Glu Pro Thr Ala Asp Gly Met Lys Val Tyr
        355                 360                 365

Gly Lys Gln Thr Leu Lys Gly Gly Ala Ala Val Ser Ser His Gly Asp
    370                 375                 380

His Arg Ile Gly Met Met Leu Gly Ile Ala Ser Cys Ile Thr Glu Glu
385                 390                 395                 400

Pro Ile Glu Ile Glu His Thr Asp Ala Ile His Val Ser Tyr Pro Thr
                405                 410                 415

Phe Phe Glu His Leu Asn Lys Leu Ser Lys Lys Ser
            420                 425

<210> SEQ ID NO 12
<211> LENGTH: 444
<212> TYPE: PRT
<213> ORGANISM: Escherichia coli

<400> SEQUENCE: 12

Ala Gly Ala Glu Glu Ile Val Leu Gln Pro Ile Lys Glu Ile Ser Gly
1               5                   10                  15

Thr Val Lys Leu Pro Gly Ser Lys Ser Leu Ser Asn Arg Ile Leu Leu
            20                  25                  30

Leu Ala Ala Leu Ser Glu Gly Thr Thr Val Val Asp Asn Leu Leu Asn
        35                  40                  45

Ser Glu Asp Val His Tyr Met Leu Gly Ala Leu Arg Thr Leu Gly Leu
    50                  55                  60

Ser Val Glu Ala Asp Lys Ala Ala Lys Arg Ala Val Val Val Gly Cys
65                  70                  75                  80

Gly Gly Lys Phe Pro Val Glu Asp Ala Lys Glu Val Gln Leu Phe
                85                  90                  95

Leu Gly Asn Ala Gly Thr Ala Met Arg Pro Leu Thr Ala Ala Val Thr
                100                 105                 110

Ala Ala Gly Gly Asn Ala Thr Tyr Val Leu Asp Gly Val Pro Arg Met
            115                 120                 125

Arg Glu Arg Pro Ile Gly Asp Leu Val Val Gly Leu Lys Gln Leu Gly
        130                 135                 140

Ala Asp Val Asp Cys Phe Leu Gly Thr Asp Cys Pro Pro Val Arg Val
145                 150                 155                 160
```

```
Asn Gly Ile Gly Gly Leu Pro Gly Gly Lys Val Lys Leu Ser Gly Ser
            165                 170                 175

Ile Ser Ser Gln Tyr Leu Ser Ala Leu Leu Met Ala Ala Pro Leu Ala
            180                 185                 190

Leu Gly Asp Val Glu Ile Glu Ile Asp Lys Leu Ile Ser Ile Pro
            195                 200                 205

Tyr Val Glu Met Thr Leu Arg Leu Met Glu Arg Phe Gly Val Lys Ala
            210                 215                 220

Glu His Ser Asp Ser Trp Asp Arg Phe Tyr Ile Lys Gly Gly Gln Lys
225                 230                 235                 240

Tyr Lys Ser Pro Lys Asn Ala Tyr Val Glu Gly Asp Ala Ser Ser Ala
            245                 250                 255

Ser Tyr Phe Leu Ala Gly Ala Ala Ile Thr Gly Thr Val Thr Val
            260                 265                 270

Glu Gly Cys Gly Thr Thr Ser Leu Gln Gly Asp Val Lys Phe Ala Glu
            275                 280                 285

Val Leu Glu Met Met Gly Ala Lys Val Thr Trp Thr Glu Thr Ser Val
            290                 295                 300

Thr Val Thr Gly Pro Pro Arg Glu Pro Phe Gly Arg Lys His Leu Lys
305                 310                 315                 320

Ala Ile Asp Val Asn Met Asn Lys Met Pro Asp Val Ala Met Thr Leu
            325                 330                 335

Ala Val Val Ala Leu Phe Ala Asp Gly Pro Thr Ala Ile Arg Asp Val
            340                 345                 350

Ala Ser Trp Arg Val Lys Glu Thr Glu Arg Met Val Ala Ile Arg Thr
            355                 360                 365

Glu Leu Thr Lys Leu Gly Ala Ser Val Glu Glu Gly Pro Asp Tyr Cys
            370                 375                 380

Ile Ile Thr Pro Pro Glu Lys Leu Asn Val Thr Ala Ile Asp Thr Tyr
385                 390                 395                 400

Asp Asp His Arg Met Ala Met Ala Phe Ser Leu Ala Ala Cys Ala Glu
            405                 410                 415

Val Pro Val Thr Ile Arg Asp Pro Gly Cys Thr Arg Lys Thr Phe Pro
            420                 425                 430

Asp Tyr Phe Asp Val Leu Ser Thr Phe Val Lys Asn
            435                 440

<210> SEQ ID NO 13
<211> LENGTH: 427
<212> TYPE: PRT
<213> ORGANISM: Zea mays

<400> SEQUENCE: 13

Met Glu Ser Leu Thr Leu Gln Pro Ile Ala Arg Val Asp Gly Thr Ile
1               5                   10                  15

Asn Leu Pro Gly Ser Lys Ser Val Ser Asn Arg Ala Leu Leu Leu Ala
            20                  25                  30

Ala Leu Ala His Gly Lys Thr Val Leu Thr Asn Leu Leu Asp Ser Asp
            35                  40                  45

Asp Val Arg His Met Leu Asn Ala Leu Thr Ala Leu Gly Val Ser Tyr
            50                  55                  60

Thr Leu Ser Ala Asp Arg Thr Arg Cys Glu Ile Ile Gly Asn Gly Gly
65                  70                  75                  80

Pro Leu His Ala Glu Gly Ala Leu Glu Leu Phe Leu Gly Asn Ala Gly
            85                  90                  95
```

```
Thr Ala Met Arg Pro Leu Ala Ala Ala Leu Cys Leu Gly Ser Asn Asp
            100                 105                 110

Ile Val Leu Thr Gly Glu Pro Arg Met Lys Glu Arg Pro Ile Gly His
        115                 120                 125

Leu Val Asp Ala Leu Arg Leu Gly Gly Ala Lys Ile Thr Tyr Leu Glu
    130                 135                 140

Gln Glu Asn Tyr Pro Pro Leu Arg Leu Gln Gly Gly Phe Thr Gly Gly
145                 150                 155                 160

Asn Val Asp Val Asp Gly Ser Val Ser Gln Phe Leu Thr Ala Leu
                165                 170                 175

Leu Met Thr Ala Pro Leu Ala Pro Glu Asp Thr Val Ile Arg Ile Lys
            180                 185                 190

Gly Asp Leu Val Ser Lys Pro Tyr Ile Asp Ile Thr Leu Asn Leu Met
        195                 200                 205

Lys Thr Phe Gly Val Glu Ile Glu Asn Gln His Tyr Gln Gln Phe Val
    210                 215                 220

Val Lys Gly Gly Gln Ser Tyr Gln Ser Pro Gly Thr Tyr Leu Val Glu
225                 230                 235                 240

Gly Asp Ala Ser Ser Ala Ser Tyr Phe Leu Ala Ala Ala Ile Lys
                245                 250                 255

Gly Gly Thr Val Lys Val Thr Gly Ile Gly Arg Asn Ser Met Gln Gly
            260                 265                 270

Asp Ile Arg Phe Ala Asp Val Leu Glu Lys Met Gly Ala Thr Ile Cys
        275                 280                 285

Trp Gly Asp Asp Tyr Ile Ser Cys Thr Arg Gly Glu Leu Asn Ala Ile
    290                 295                 300

Asp Met Asp Met Asn His Ile Pro Asp Ala Ala Met Thr Ile Ala Thr
305                 310                 315                 320

Ala Ala Leu Phe Ala Lys Gly Thr Thr Thr Leu Arg Asn Ile Tyr Asn
                325                 330                 335

Trp Arg Val Lys Glu Thr Asp Arg Leu Phe Ala Met Ala Thr Glu Leu
            340                 345                 350

Arg Lys Val Gly Ala Glu Val Glu Glu Gly His Asp Tyr Ile Arg Ile
        355                 360                 365

Thr Pro Pro Glu Lys Leu Asn Phe Ala Glu Ile Ala Thr Tyr Asn Asp
    370                 375                 380

His Arg Met Ala Met Cys Phe Ser Leu Val Ala Leu Ser Asp Thr Pro
385                 390                 395                 400

Val Thr Ile Leu Asp Pro Lys Cys Thr Ala Lys Thr Phe Pro Asp Tyr
                405                 410                 415

Phe Glu Gln Leu Ala Arg Ile Ser Gln Ala Ala
            420                 425

<210> SEQ ID NO 14
<211> LENGTH: 1305
<212> TYPE: DNA
<213> ORGANISM: Artificial Sequence
<220> FEATURE:
<223> OTHER INFORMATION: syngrg32

<400> SEQUENCE: 14
atgacggcgt cggcaagctg gacggcaagg aagggccagc cgctgcaagg aagcctcacc      60
atccccggcg acaagagcgt cagccaccgc gccgtgatgt cgccgcgct cgccgacggc     120 gtcagccaca ttgatggctt cctagaagga gaagatacaa gggccaccgc cgccatcttc     180
```

-continued

```
tctcaaatgg gcgtcaggat tgagacgccg tcgccaagcc aaagaattgt tcatggcgtc    240
ggcgtggatg gactacaagc gccggcgggg ccgctggact gcggcaacgc cggcaccggc    300
atgaggctgc tggctgggct gctggcggcg cagccatttg atgctgtgat ggtgggagat    360
gaaagcctca gccggcggcc aatgaggagg gtgacagggc cgctggctca aatgggcgcc    420
aagatcgaca cagaagctga tgggacgccg ccgctacgag ttcatggagg gcagccgctg    480
catggcatcg acttcgcctc gccggtggcc tcggcgcagg tcaagagcgc cgtgctgctg    540
gccggcctct atgctcaagg agaaacttct gtgacagaac ctcatccaac aagggactac    600
tcagaaagga tgctcagggc cttcggcgtg gagattgagt tctcgccggg caaggcaagg    660
ctccgcggcg gccagaggct gagggccacc gacatcgccg tgccggcgga cttctcctcc    720
gccgccttct tcctggtggc ggcaagcatc atccctggct cggcgctcac cctccgtcaa    780
gttggcctca acccgcggcg caccggccta ctggcggcgc tgccggctgat gggcgccgac    840 atcagggagg agaaccatgc tgagcaagga ggagaagccg tcgccgacct ggtggtgcgg    900
catgctcctc ttcatggcgc cgagatcccg gaggcgctgg tgccggacat gattgatgag    960
ttcccggcgc tcttcgtggc ggcggcggcg gctcaaggca acaccatcgt ccgcggcgcc   1020
gccgagctac gcgtcaagga gagcgacagg ctggcggcaa tggccaccgg cctgaggagc   1080
ctcggcgtgc aagttgatga aacagaagat ggcgccacca tccacggcgg ccatgagctg   1140
ggcagcggca ccatcgagag tcatggagat cacaggattg caatggcctt cgccatcgcc   1200
ggccagctct caagtggaga ggtgaggatc aacgacatcg ccaatgtggc caccagcttc   1260
cccaacttcg acggcattgc aaggacggcg ggcttcaacc tcggc                   1305
```